US009403865B2

(12) United States Patent
Cedillo et al.

(10) Patent No.: US 9,403,865 B2
(45) Date of Patent: Aug. 2, 2016

(54) METHOD OF PREPARING OLIGOMERIC COMPOUNDS USING MODIFIED CAPPING PROTOCOLS

(71) Applicants: Isis Pharmaceuticals, Inc., Carlsbad, CA (US); Genzyme Corporation, Cambridge, MA (US)

(72) Inventors: Isaiah E. Cedillo, Vista, CA (US); Darren Janczak, Temecula, CA (US); Phillip Michael Weaver, Suffolk (GB)

(73) Assignees: Ionis Pharmaceuticals, Inc., Carlsbad, CA (US); Genzyme Corporation, Cambridge, MA (US)

(*) Notice: Subject to any disclaimer, the term of this patent is extended or adjusted under 35 U.S.C. 154(b) by 0 days.

(21) Appl. No.: 14/417,601

(22) PCT Filed: Aug. 15, 2013

(86) PCT No.: PCT/US2013/055146
§ 371 (c)(1),
(2) Date: Jan. 27, 2015

(87) PCT Pub. No.: WO2014/028739
PCT Pub. Date: Feb. 20, 2014

(65) Prior Publication Data
US 2015/0218205 A1 Aug. 6, 2015

Related U.S. Application Data

(60) Provisional application No. 61/683,546, filed on Aug. 15, 2012.

(51) Int. Cl.
*C07H 21/00* (2006.01)
*C07H 21/04* (2006.01)
*C07H 1/00* (2006.01)

(52) U.S. Cl.
CPC .................. *C07H 21/04* (2013.01); *C07H 1/00* (2013.01); *C07H 21/00* (2013.01)

(58) Field of Classification Search
None
See application file for complete search history.

(56) References Cited

U.S. PATENT DOCUMENTS

| 3,687,808 | A | 8/1972 | Merigan et al. |
|---|---|---|---|
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lableu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,069 | E | 9/1992 | Koster et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |

(Continued)

FOREIGN PATENT DOCUMENTS

| EP | 0984021 | 3/2000 |
|---|---|---|
| WO | WO 90/02749 | 3/1990 |

(Continued)

OTHER PUBLICATIONS

Hudson et al. J. Am. Chem. Soc. (1993), vol. 115, pp. 2119-2124.*
Horn et al. Nucleic Acids Research (1989), vol. 17, pp. 6959-6967.*
Ravikumar et al. Organic Process Research & Development (2008), vol. 12, pp. 399-410.*
Wincott et al. Nucleic Acids Research (1995), vol. 23, pp. 2677-2684.*
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Patrick Lewis
(74) *Attorney, Agent, or Firm* — McNeill Baur PLLC

(57) ABSTRACT

Provided herein are methods for the solid phase synthesis of oligomeric compounds wherein at least one of the capping steps has been modified. More particularly, methods are provided wherein one or more of the capping steps is omitted or performed using reduced equivalents of acetic anhydride. In certain embodiments, the methods provide an enhanced purity profile. In certain embodiments, the methods provide an increased yield. The methods provided herein also provide at least an economic advantage over currently used methods in that reduced amounts of the mixture of capping reagents are required.

22 Claims, 9 Drawing Sheets

(56) References Cited

U.S. PATENT DOCUMENTS

| | | | |
|---|---|---|---|
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,069,243 A * | 5/2000 | Scozzari ............... C07H 21/00 536/25.34 |
| 6,268,490 B1 | 7/2001 | Imanishi et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,867,294 B1 | 3/2005 | Sanghvi et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,741,457 B2 | 6/2010 | Seth et al. |
| 8,501,805 B2 | 8/2013 | Seth et al. |
| 8,530,640 B2 | 9/2013 | Migawa et al. |
| 8,546,556 B2 | 10/2013 | Seth et al. |
| 9,012,421 B2 | 4/2015 | Migawa et al. |
| 2003/0045698 A1 | 3/2003 | Manoharan et al. |
| 2003/0158403 A1 | 8/2003 | Manoharan et al. |
| 2005/0130923 A1 | 6/2005 | Bhat et al. |
| 2008/0039618 A1 | 2/2008 | Allerson et al. |
| 2009/0203132 A1 | 8/2009 | Swayze et al. |
| 2012/0184724 A1 | 7/2012 | Sierzchala et al. |

FOREIGN PATENT DOCUMENTS

| | | |
|---|---|---|
| WO | WO 92/07864 | 5/1992 |
| WO | WO 98/39352 | 9/1998 |
| WO | WO 99/14226 | 3/1999 |
| WO | WO 01/49687 | 7/2001 |
| WO | WO 2004/106356 | 12/2004 |
| WO | WO 2005/021570 | 3/2005 |
| WO | WO 2005/121371 | 12/2005 |
| WO | WO 2005/121372 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |

OTHER PUBLICATIONS

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O- Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure—activity relationships and the design of improved signal-transduction inhibitors" Biochem. Soc. Trans. (1996) 24:630-637.

Alul et al., "Oxalyl-CPG: a labile support for synthesis of sensitive oligonucleotide derivatives" Nucleic Acid Research (1991) 19(7):1527.

Atherton et al., "Peptide synthesis. Part 2. Procedures for solid-phase synthesis using Nα-fluorenylmethoxycarbonylamino-acids on polyamide supports. Synthesis of substance P and of acyl carrier protein 65-74 decapeptide" J. Chem. Soc. Perkin Trans. I (1981) 538-546.

Atherton et al., "Polyamide supports for polypeptide synthesis" J. Am. Chem. Soc. (1975) 97(22):6584-6585.

Atherton et al., "The polyamide method of solid phase peptide and oligonucleotides synthesis" Bioorg. Chem. (1979) 8(3):351-370.

(56) References Cited

OTHER PUBLICATIONS

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.
Bayer et al. "A new support for polypeptide synthesis in columns" Tetrahedron Letters (1970) 11(51):4503-4505.
Beaucage et al., "Advances in the Synthesis of Oligonucleotides by the Phosphoramidite Approach" Tetrahedron (1992) 48(12):2223-2311.
Beaucage et al., "Deoxynucleoside Phosphoramidites—A New Class of Key Intermediates for Deoxypolynucleotide Synthesis" Tetrahedron Letters (1981) 22(20):1859-1862.
Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phosphoiylated Biomolecules by the Phosphoramidite Method" Tetrahedron (1993) 49(46):10441-10488.
Berg et al., "Long-Chain Polystyrene-Grafted Polyethylene Film Matrix: A New Support for Solid-Phase Peptide Synthesis" J. Am. Chem. Soc. (1989) 111:8024-8026.
Bonora et al., "A Liquid-Phase Process Suitable for Large-Scale Synthesis of Phosphorothioate Oligonucleotides" Organic Process Research & Development (2000) 4:225-231.
Braasch et al., "Locked nucleic acid (LNA): fine-tuning the recognition of DNA and RNA" Chem. Biol. (2001) 8:1-7.
Capaldi et al., Antisense Drug Discovery: Princples, Strategies and Applications, Crooke ed., CRC Press (2007) 401-434.
Daniels et al., "Membranes as Solid Supports for Peptide Synthesis" Tetrahedron Letters (1989) 30(33);4345-4348.
Eadie et al., "Guanine modification during chemical DNA synthesis" Nucleic Acid Research (1987) 15(20):8333-8349.
Eichler et al., "Application of Cellulose Paper as Support Material in Simultaneous Solid Phase Peptide Synthesis" Collect. Czech. Chem. Commun. (1989) 54:1746-1752.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Geysen et al., "Use of peptide synthesis to probe viral antigens for epitopes to a resolution of a single amino acid" Proc. Natl. Acad. Sci. (1984) 81:3998-4002.
Gorman, "An Apparatus for Simultaneous Manual Solid Phase Synthesis of Multiple Peptide Analogs" Anal. Biochem. (1984) 136:397-406.
Gravert et al., "Organic Synthesis on Soluble Polymer Supports: Liquid-Phase Methodologies" Chem. Rev. (1997) 97(2):489-510.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Horvath et al., "Stereoselective synthesis of (—)-ara-cyclohexenyl-adenine" Tetrahedron Letters (2007) 48:3621-3623.
Houghten, "General method for the rapid solid phase synthesis of large numbers of peptides: Specificity of antigen antibody interaction at the level of individual amino acids" Proc. Natl. Acad. Sci. (1985) 82:5131-5135.
Jin et al., "Stereoselective Synthesis of Dithymidine Phosphorothioates Using Xylose Derivatives as Chiral Auxiliaries" J. Org. Chem. (1997) 63:3647-3654.
Kent et al., "Preparation and Properties of tert-Butyloxycarbonylaminoacyl-4-(oxymethyl) phenylacetamidomethyl-(Kel F-g-styrene) Resin, an Insoluble, Noncrosslinked Support for Solid Phase Peptide Synthesis" Israel J. Chem. (1978) 17(4):243-247.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Krchnak et al., "Multiple continuous-flow solid-phase peptide synthesis" Int. J. Peptide Protein Res. (1989) 33:209-213.
Kumar et al., "The first analogues of LNA (locked nucleic acids): phosphorothioate-LNA and 2'-thio-LNA" Bioorg Med Chem Lett. (1998) 8:2219-2222.
Lebl et al., "Simulation of Continuous Solid Phase Synthesis: Synthesis of Methionine Enkephalin and its Analogs" Peptide Res. (1989) 2(4):297-300.
Leumann et al., "DNA Analogues: From Supramolecular Principles to Biological Properties" Bioorganic & Medicinal Chemistry (2002) 10:841-854.
Martin, "Ein neuer Zugang zu 2'-O-Alkylribonucleosiden and Eigenschaften deren Oligonucleotide" Hely. Chim. Acta. (1995) 78(2):486-504.
McBride et al., "An Investigation of Several Deoxynucleoside Phosphoramidites Useful for Synethesizing Deoxyoligonucleotides" Tetrahedron Letters (1983) 24(3):245-248.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
Orum et al., "Locked nucleic acids: A promising molecular family for gene-function analysis and antisense drug development" Curr. Opinion Mol. Ther. (2001) 3:239-243.
Parr et al. "Solid-Phase Peptide Synthesis on an Inorganic Matrix having Organic Groups on the Surface" Chem. Internal. Ed. (1972) 11:314.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Ciyst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Sanghvi, "Heterocyclic base modifications in nucleic acids and their applications in antisense oligonucleotides" Antisense Research and Applications, Crooke and Lebleu ed., CRC Press (1993) 273-302.
Sanghvi, Chapter 15, Antisense Research and Applications, Crooke and Lebleu ed., CRC Press (1993).
Scaringe, "RNA Oligonucleotide Synthesis via 5'-Sily1-2'-Orthoester Chemistry" Methods (2001) 23:206-217.
Scott et al., "The Use of Resin Coated Glass Beads in the Form of a Packed Bed for the Solid Phase Synthesis of Peptides" J. Chrom. Sci. (1971) 9(10):577-591.
Singh et al., "LNA (locked nucleic acids): synthesis and high-affinity nucleic acid recognition" Chem. Commun. (1998) 455-456.

(56) References Cited

OTHER PUBLICATIONS

Singh et al., "Synthesis of 2'-amino-LNA: A novel conformationally restricted high-affinity oligonucleotide analogue with a handle" J. Org. Chem. (1998) 63: 10035-10039.

Sinha et al., "Polymer support oligonucleotide synthesis XVIII: use of beta-cyanoethyl-N,N-dialkylamino/N-morpholino phosphoramidite of deoxynucleosides for the synthesis of DNA fragments simplifying deprotection and isolation of the final product" Nucleic Acid Research (1984) 12(11):4539-4557.

Srivastava et al., "Five- and Six-Membered Conformationally Locked 2',4'-Carbocyclic riboThymidines: Synthesis, Structure, and Biochemical Studies" J. Am. Chem. Soc. (2007) 129(26):8362-8379.

Tregear, "Graft Copolymers as Insoluble Supports in Peptide Synthesis" Chemistry and Biology of Peptides, J. Meienhofer, Ed., Ann Arbor Sci. Publ., Ann Arboer, 1972, pp. 175-178.

Swayze et al., The Medicinal Chemistry of Oligonucleotides in Antisense a Drug Technology, Chapter 6, pp. 143-182, Crooke, S.T., ed., 2008.

Verbeure et al., "RNase H mediated cleavage of RNA by cyclohexene nucleic acid (CeNA)" Nucleic Acids Res. (2001) 29(24):4941-4947.

Wahlestedt et al., "Potent and nontoxic antisense oligonucleotide containing locked nucleic acids" Proc. Natl. Acad. Sci. USA (2000) 97: 5633-5638.

Wang et al., "A stereoselective synthesis of dinucleotide phosphorothioate triesters through a chiral indoloxazaphosphorine intermediate" Tetrahedron Letters (1997) 38(5):705-708.

Wang et al., "A stereoselective synthesis of dinucleotide phosphorothioates, using chiral indoloxazaphosphorine intermediates" Tetrahedron Letters (1997) 38(22):3797-3800.

Wang et al., "A straightforward stereoselective synthesis of D- and L-5-hydroxy-4-hydroxymethyl-2-cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Wright et al. "Large scale synthesis of oligonucleotides via phosphoramidite nucleosides and a high-loaded polystyrene support" Tetrahedron Letters (1993) 34(21):3373-3376.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

* cited by examiner

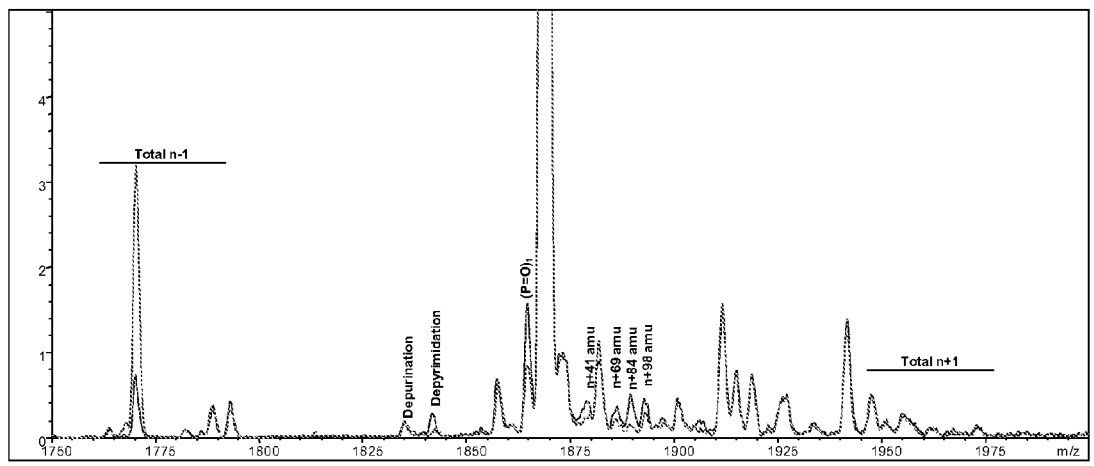
Figure 1. Overlay of average mass spectra under main UV peaks for the comparison of Method B (no capping) to the control Method A (standard capping) for 5-10-5 MOE gapmer-1 on a 2.0 mmol scale
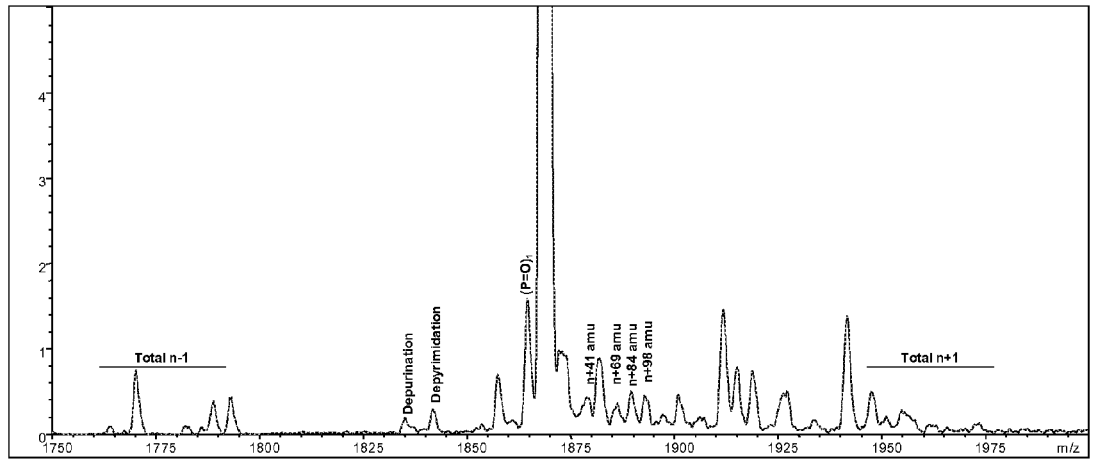
Figure 2. Average mass spectra under main UV peaks for 5-10-5 MOE gapmer-1 on a 2.0 mmol scale using Method A (standard capping)

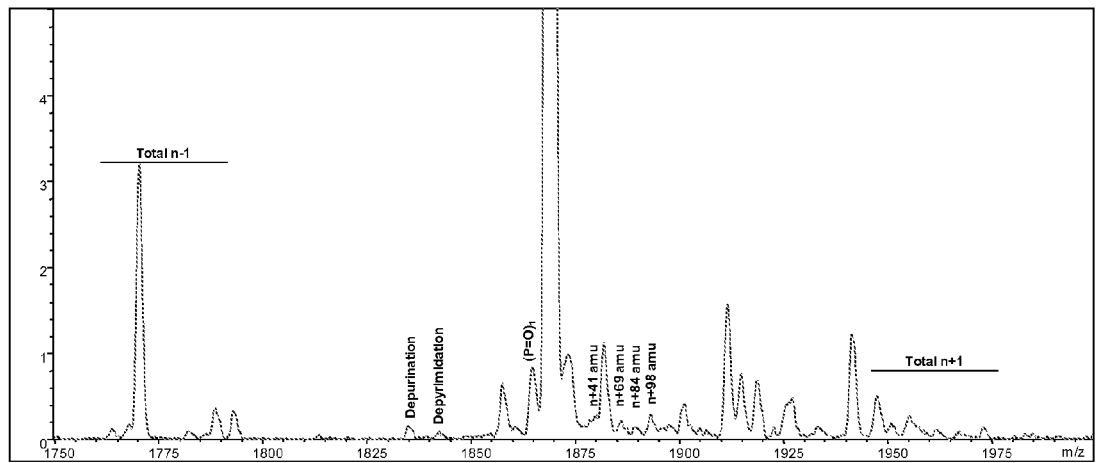
Figure 3. Average mass spectra under main UV peaks for 5-10-5 MOE gapmer-1 on a 2.0 mmol scale using Method B (no capping)
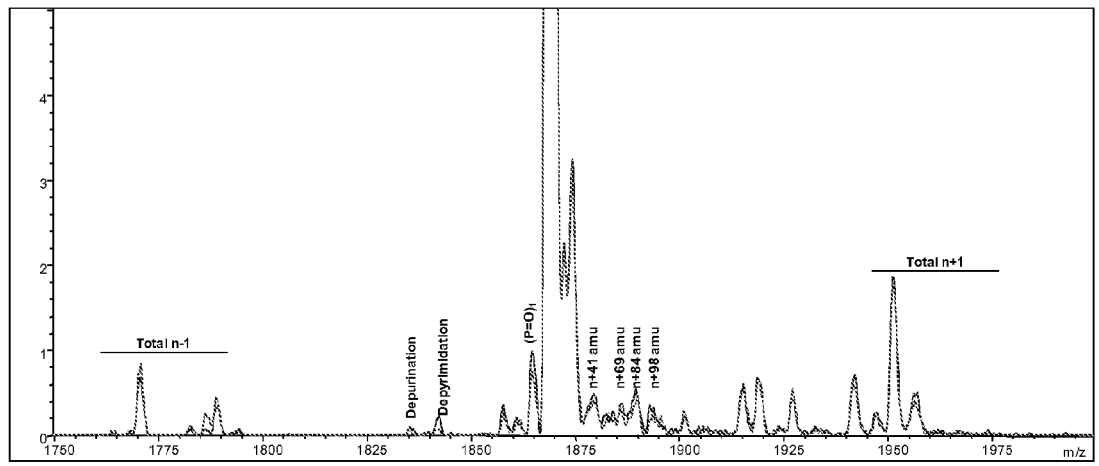
Figure 4. Overlay of average mass spectra under main UV peaks for the comparison of Method C (1/2 capping) to the control Method A (standard capping) for 5-10-5 MOE gapmer-1 on a 550 mmol scale

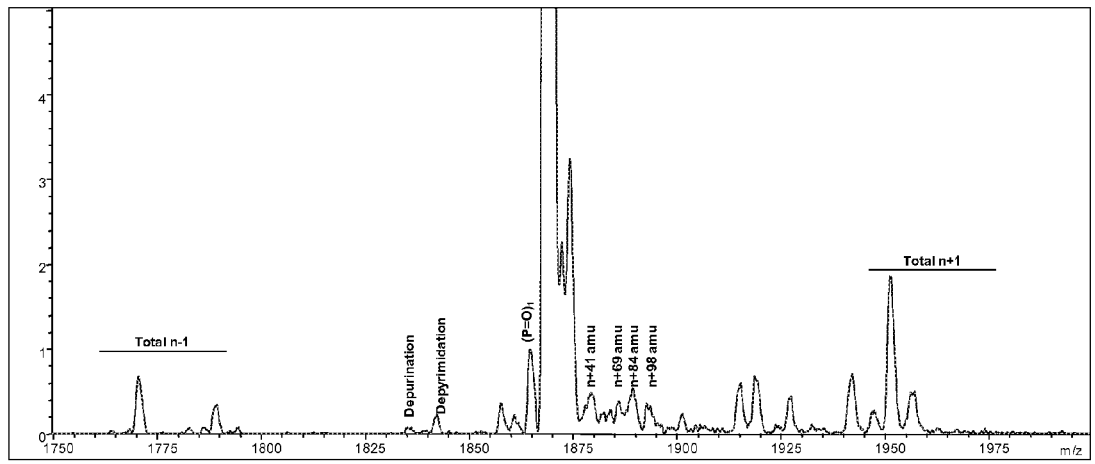
Figure 5. Average mass spectra under main UV peaks for 5-10-5 MOE gapmer-1 on a 550 mmol scale using Method A (standard capping)
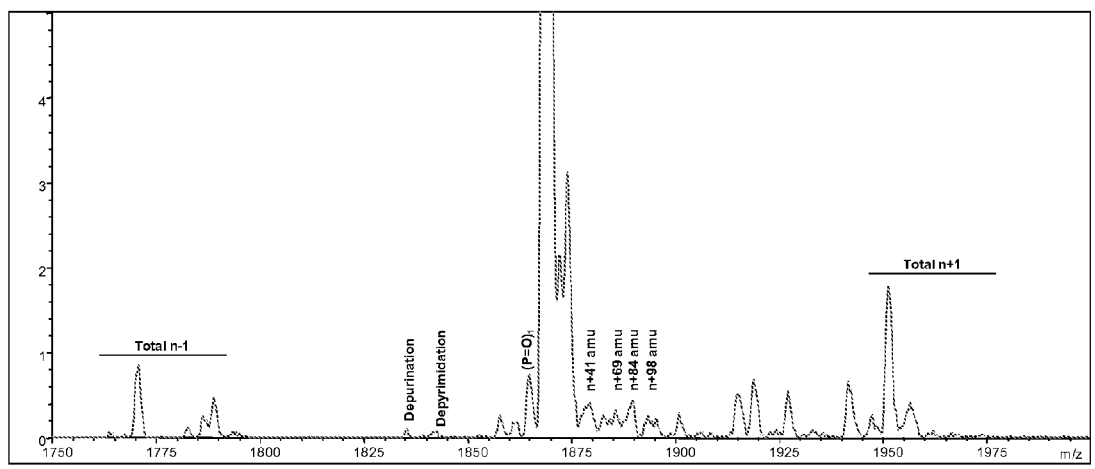
Figure 6. Average mass spectra under main UV peaks for 5-10-5 MOE gapmer-1 on a 550 mmol scale using Method C (1/2 capping)

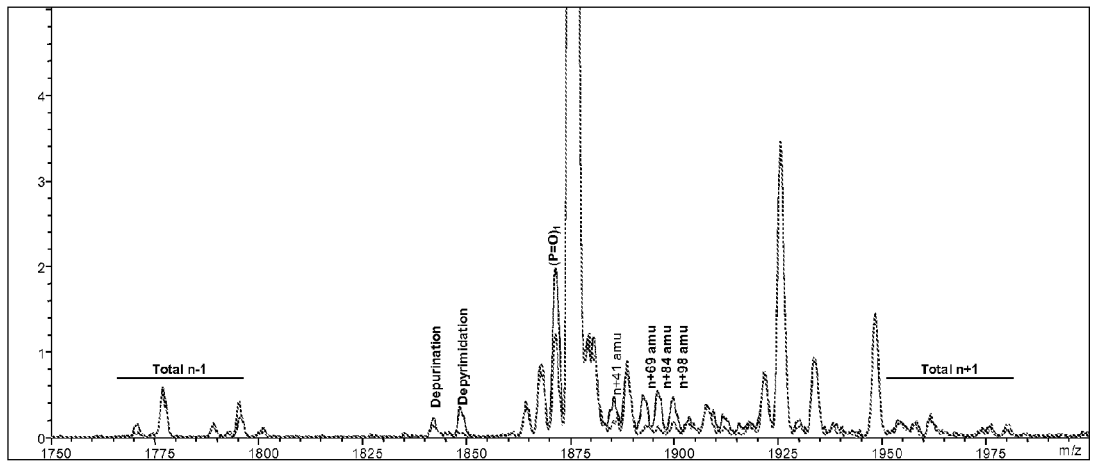
Figure 7. Overlay of average mass spectra under main UV peaks for the comparison of Method B (no capping) to the control Method A (standard capping) for 5-10-5 MOE gapmer-2 on a 2.0 mmol scale
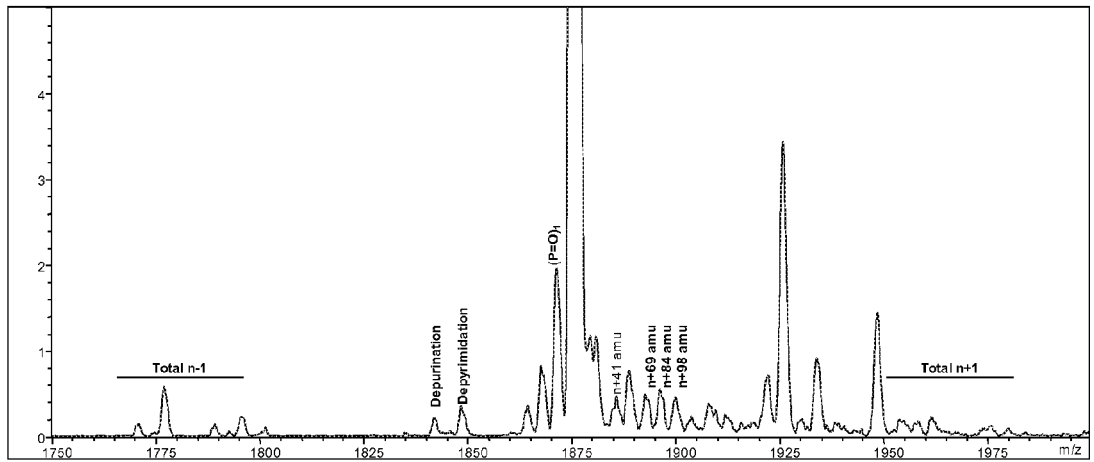
Figure 8. Average mass spectra under main UV peaks for 5-10-5 MOE gapmer-2 on a 2.0 mmol scale using Method A (standard capping)

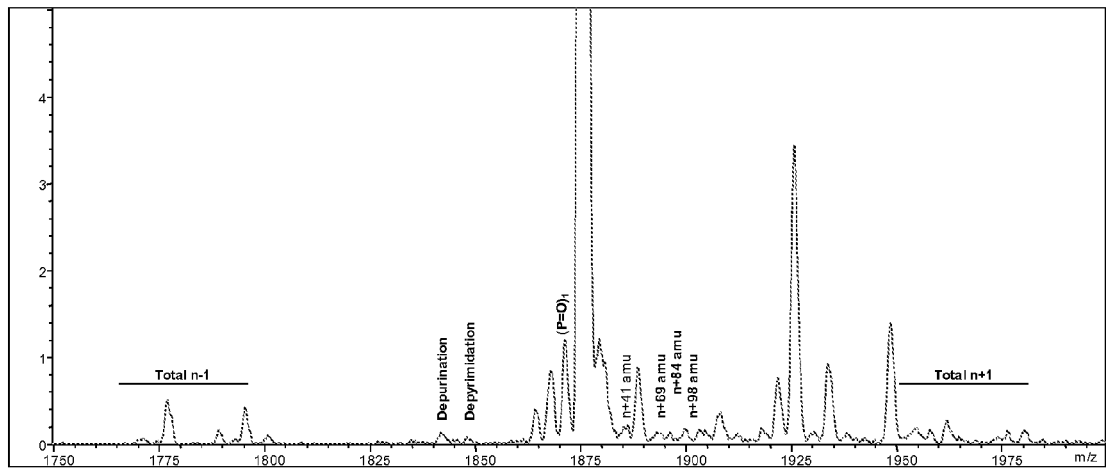
Figure 9. Average mass spectra under main UV peaks for 5-10-5 MOE gapmer-2 on a 2.0 mmol scale using Method B (no capping)
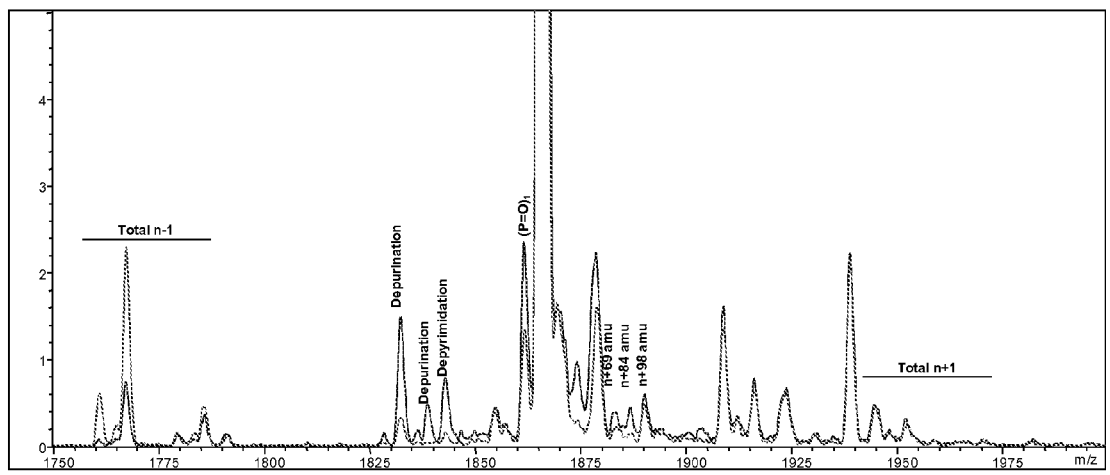
Figure 10. Overlay of average mass spectra under main UV peaks for the comparison of Method D (no capping except for UnyLinker) to the control Method A (standard capping) for 5-10-5 MOE gapmer-3 on a 2.0 mmol scale

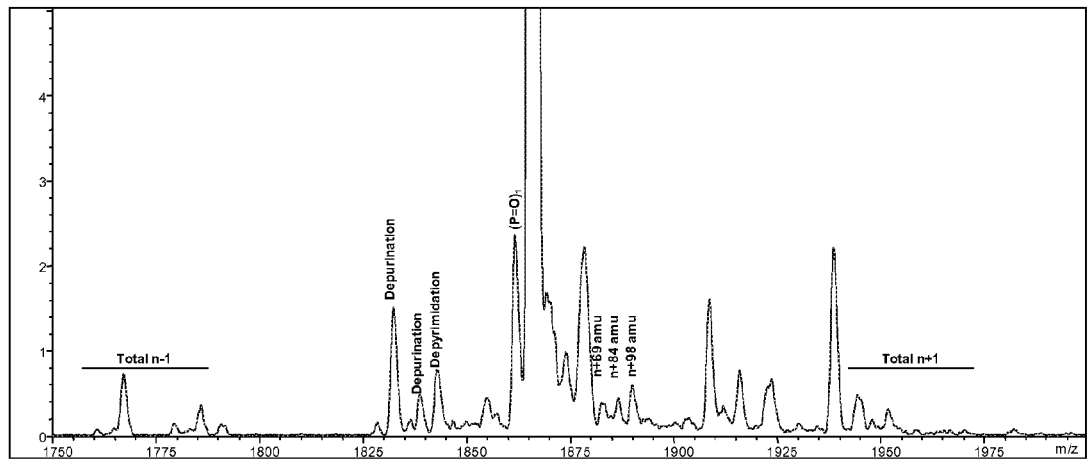
Figure 11. Average mass spectra under main UV peaks for 5-10-5 MOE gapmer-3 on a 2.0 mmol scale using Method A (standard capping)
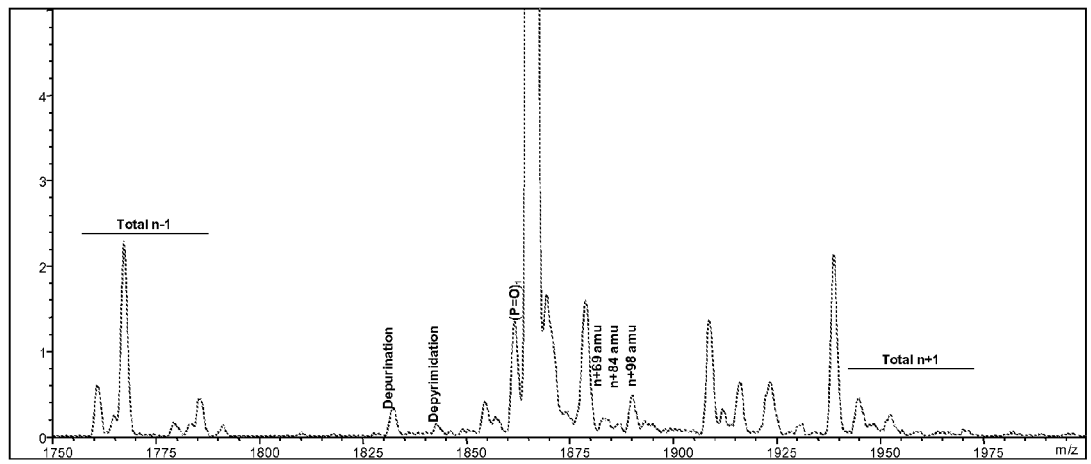
Figure 12. Average mass spectra under main UV peaks for 5-10-5 MOE gapmer-3 on a 2.0 mmol scale using Method D (no capping except for Unylinker)

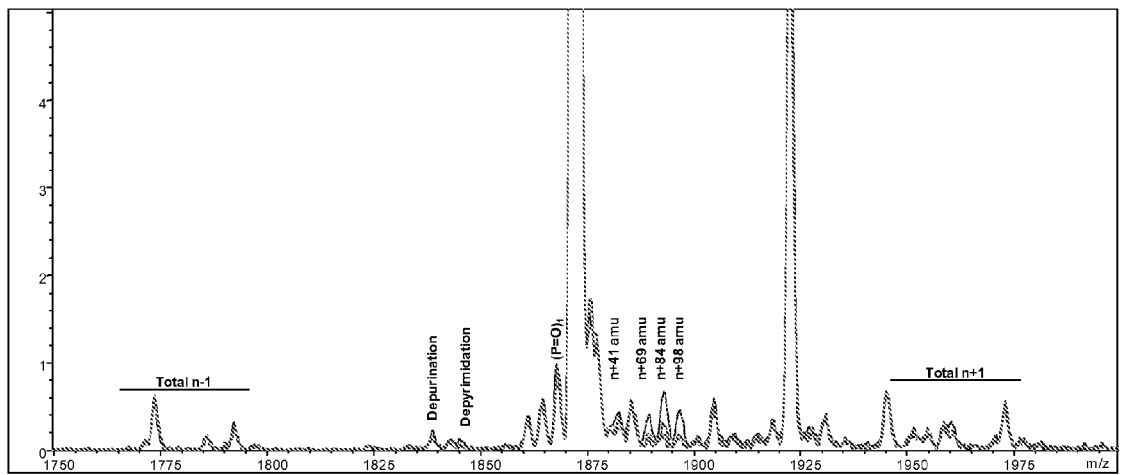
Figure 13. Overlay of average mass spectra under main UV peaks for the comparison of Method B (no capping), Method C (1/2capping) and Method E (1/4 capping) to the control Method A (standard capping) for 5-10-5 MOE gapmer-4 on a 2.0 mmol scale
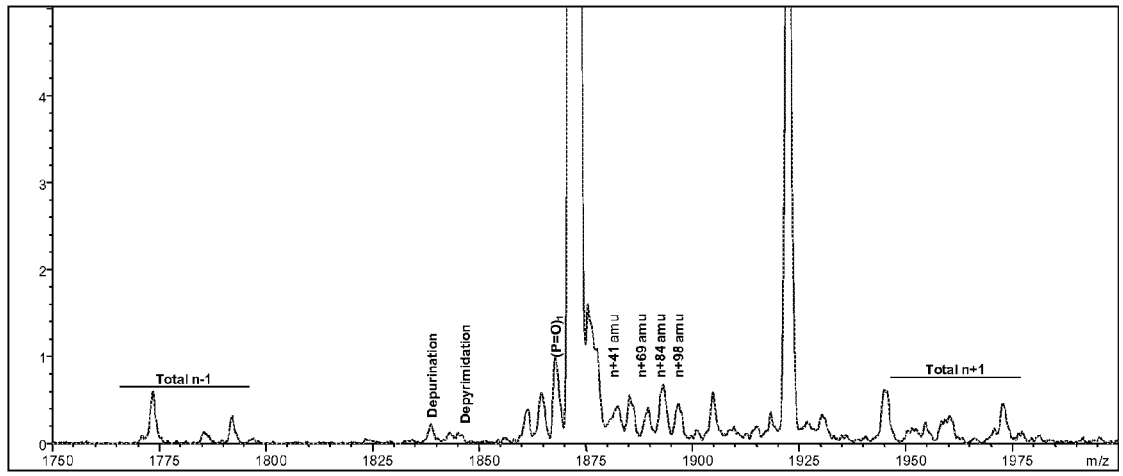
Figure 14. Average mass spectra under main UV peaks for 5-10-5 MOE gapmer-4 on a 2.0 mmol scale using Method A (standard capping)

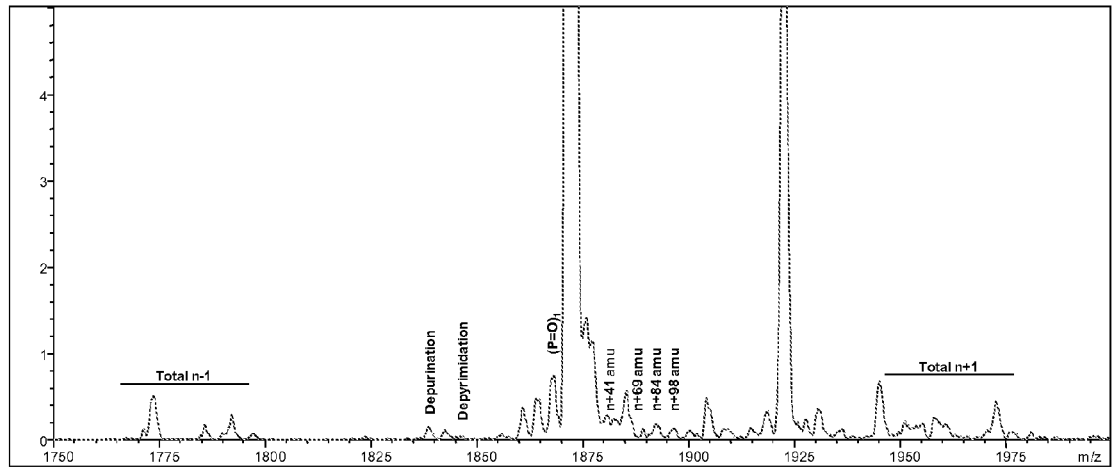
Figure 15. Average mass spectra under main UV peaks for 5-10-5 MOE gapmer-4 on a 2.0 mmol scale using Method B (no capping)
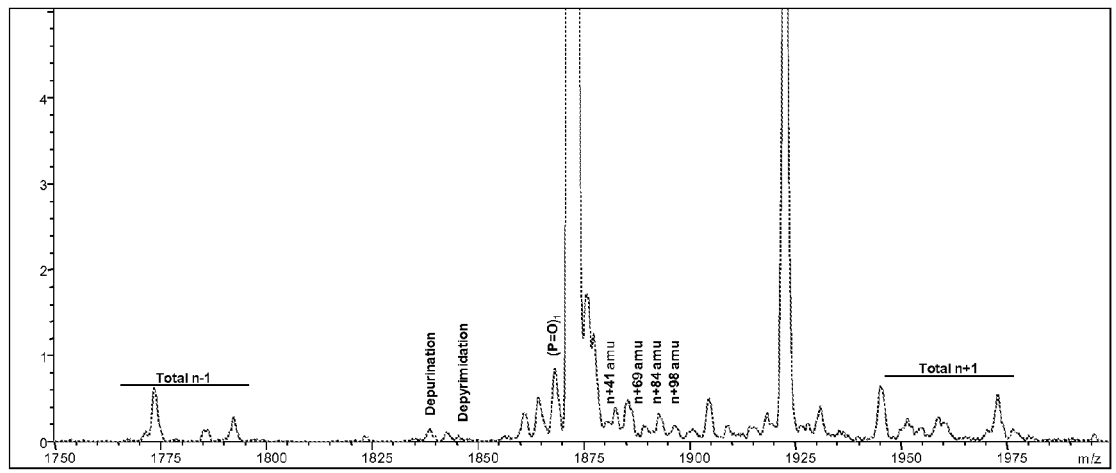
Figure 16. Average mass spectra under main UV peaks for 5-10-5 MOE gapmer-4 on a 2.0 mmol scale using Method C (1/2 capping)

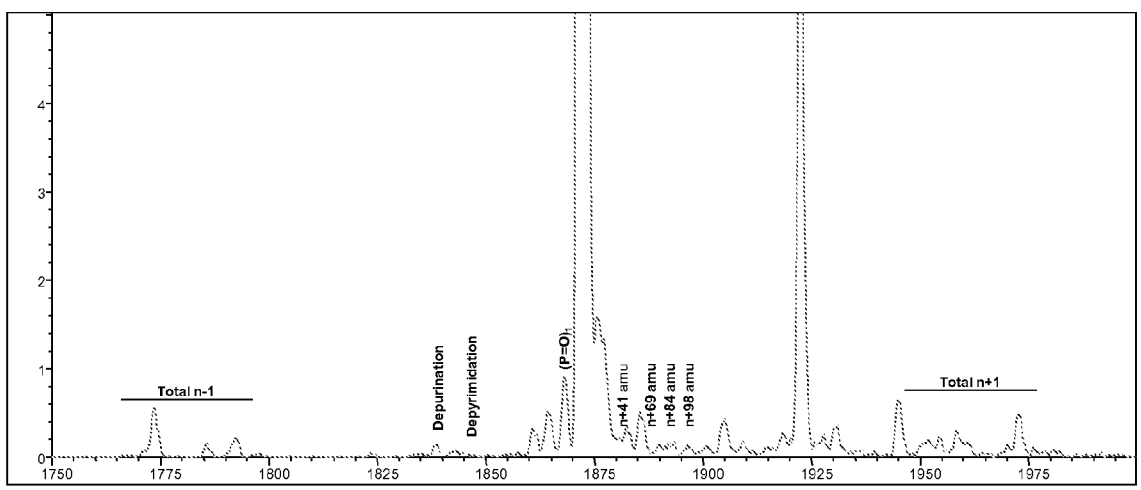
Figure 17. Average mass spectra under main UV peaks for 5-10-5 MOE gapmer-4 on a 2.0 mmol scale using Method E (1/4 capping)

METHOD OF PREPARING OLIGOMERIC COMPOUNDS USING MODIFIED CAPPING PROTOCOLS

CROSS REFERENCED TO RELATED APPLICATIONS

This application is a U.S. National Phase filing under 35 U.S.C. §371 claiming priority to International Serial No. PCT/US2013/055146 filed Aug. 15, 2013, which claims priority to U.S. Provisional Application 61/683,546, filed Aug. 15, 2012, each of which is incorporated herein by reference in its entirety.

FIELD OF THE INVENTION

The present disclosure is directed to the field of oligomer synthesis. In particular, improvements in the synthesis of oligomeric compounds are provided by modification of the capping protocols during solid phase oligomer synthesis. In certain embodiments, the improvements in solid phase synthesis of oligomeric compounds include an enhanced purity profile. In certain embodiments, the improvements in solid phase synthesis of oligomeric compounds include an increase in the yield.

BACKGROUND OF THE INVENTION

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. This widespread use of oligonucleotides has led to an increasing demand for rapid, inexpensive and efficient methods for their synthesis.

Synthetic oligonucleotides are generally prepared through the repeated coupling of nucleoside phosphoramidites to 5'-hydroxyl groups of nucleoside monomers or the free 5'-hydroxyl groups of growing oligomers. A commonly used method to perform oligomer synthesis is the phosphoramidite approach (see for example: Beaucage and Caruthers (1981) Tetrahedron Letters 22:1859-1862; McBride and Caruthers (1983) Tetrahedron Letters 24:245-248; Sinha et al. (1984) Nucleic Acids Res. 12:4539-4557 and Beaucage and Iyer (1992) Tetrahedron 48:2223-2311, each of which is incorporated herein by reference in its entirety).

SUMMARY OF THE INVENTION

Provided herein are methods of preparing oligomeric compounds wherein at least one of the capping steps is modified. Such methods are particularly amenable to automated solid phase synthesis of oligomeric compounds using phosphoramidite monomer subunits. In certain embodiments, the improvements in solid phase synthesis of oligomeric compounds include an enhanced purity profile. In certain embodiments, the improvements in solid phase synthesis of oligomeric compounds include an increase in the yield. The methods provided herein also provide at least an economic advantage over currently used methods in that reduced amounts of the mixture of capping reagents are required.

In certain embodiments, methods of preparing an oligomeric compound are provided comprising:

a) providing a solid support having a plurality of monomer subunits linked thereto wherein each of the monomer subunits comprises a blocked hydroxyl group;

b) deblocking the blocked hydroxyl groups to provide free hydroxyl groups;

c) coupling further monomer subunits to the free hydroxyl groups, wherein each further monomer subunit comprises a phosphoramidite group and a blocked hydroxyl group, to the free hydroxyl groups to provide phosphite triester linked monomer subunits;

d) oxidizing or sulfurizing the phosphite triester linked monomer subunits to provide phosphate triester or thiophosphate triester linked monomer subunits;

e) optionally treating the phosphate triester or thiophosphate triester linked monomer subunits with a mixture of capping reagents to block any unreacted free hydroxyl groups;

f) iteratively repeating steps b) through e) a predetermined number of times to provide the oligomeric compound; and wherein:

each iterative step e) is omitted; or at least one iterative step e) in addition to the last one is omitted; or at least one iterative step e) in addition to the last one is omitted and at least one iterative step e) not omitted is performed using a mixture of capping reagents having less than about 8 equivalents of acetic anhydride based on the loading of the solid support; or each iterative step e) is performed and at least one iterative step e) is performed using a mixture of capping reagents having less than about 8 equivalents of acetic anhydride based on the loading of the solid support.

In certain embodiments, the plurality of monomer subunits linked to the solid support are each linked by a 3'-ester linkage. In certain embodiments, the 3'-ester linkage is a 3'-succinyl group.

In certain embodiments, the plurality of monomer subunits linked to the solid support are each attached to a Unylinker™ functionalized solid support by a 3'-phosphite triester linkage further comprising:

oxidizing or sulfurizing each 3'-phosphite triester linkage to either a phosphate triester or a thiophosphate triester; and treating the resulting solid support linked monomer subunits with a mixture of capping reagents having 90 equivalents or less of acetic anhydride based on the loading of the solid support.

In certain embodiments, each phosphite triester is sulfurized to a thiophosphate triester. In certain embodiments, the plurality of monomer subunits linked to the solid support is treated with a mixture of capping reagents having from about 50 equivalents to about 90 equivalents of acetic anhydride based on the loading of the solid support. In certain embodiments, the plurality of monomer subunits linked to the solid support is treated with a mixture of capping reagents having from about 20 equivalents to about 50 equivalents of acetic anhydride based on the loading of the solid support.

In certain embodiments, each monomer subunit is, independently, a nucleoside or a modified nucleoside. In certain embodiments, each modified nucleoside independently comprises a furanose or modified furanose sugar group. In certain embodiments, each modified nucleoside independently comprises a substituted nucleoside, a 4'-S-modified nucleoside or a bicyclic modified nucleoside. In certain embodiments, each modified nucleoside independently comprises a 2'-substituted sugar, a 5'-substituted sugar, a 2' and 5'-substituted sugar or a 2'-4' bridged bicyclic sugar. In certain embodiments, at least one modified nucleoside comprises a sugar surrogate group.

In certain embodiments, each monomer subunit comprises a heterocyclic base moiety that is optionally protected and is independently selected from a purine, substituted purine, pyrimidine and substituted pyrimidine. In certain embodiments, each monomer subunit comprises a heterocyclic base moiety independently selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, each of the blocked hydroxyl groups is, independently, blocked with a hydroxyl blocking group selected from a substituted or unsubstituted trityl group. In certain embodiments, each hydroxyl blocking group is 4,4'-dimethoxytrityl.

In certain embodiments, each phosphoramidite group is a diisopropylcyanoethoxy phosphoramidite (—P(N[(CH)CH$_3$]$_2$)(O(CH$_2$)$_2$CN).

In certain embodiments, dichloroacetic acid in toluene is used to deblock blocked hydroxyl groups.

In certain embodiments, the methods provided herein further comprise treatment of the oligomeric compound with triethylamine in acetonitrile to remove phosphorus protecting groups thereby providing linkages between monomer subunits that are independently selected from phosphodiester and phosphorothioate. In certain embodiments, the methods provided herein further comprise treatment of the oligomeric compound with ammonium hydroxide to remove further protecting groups and cleave the oligomeric compound from the solid support.

In certain embodiments, the solid support is crosslinked polystyrene. In certain embodiments, the solid support is a crosslinked polystyrene selected from NittoPhase-HL (commercially available from H.C. Brown Pharmaceutical Research Laboratories) and Primer Support 5G (commercially available from GE Healthcare).

In certain embodiments, at least one iterative step e) in addition to the last one is omitted. In certain embodiments, iterative step e) is performed for about the first 50% of the iterative steps b) through e) and omitted for the remaining iterative steps b) through e). In certain embodiments, iterative step e) is performed for about the first 75% of the iterative steps b) through e) and omitted for the remaining iterative steps b) through e). In certain embodiments, each iterative step e) is performed.

In certain embodiments, the mixture of capping reagents used for essentially each capping step that is performed comprises about 8 equivalents of acetic anhydride based on the loading of the solid support. In certain embodiments, the mixture of capping reagents used for each capping step that is performed comprises about 6 equivalents of acetic anhydride based on the loading of the solid support. In certain embodiments, the mixture of capping reagents used for each capping step that is performed comprises about 4 equivalents of acetic anhydride based on the loading of the solid support. In certain embodiments, the mixture of capping reagents used for each capping step comprises about 2 equivalents of acetic anhydride based on the loading of the solid support. In certain embodiments, the mixture of capping reagents used for each capping step that is performed comprises less than 1 equivalent of acetic anhydride based on the loading of the solid support.

In certain embodiments, the volume of the mixture of capping reagents is modified independently for each cycle of steps b) through e) such that about 17 equivalents of acetic anhydride are used for the first cycle and over each successive cycle that includes the capping step e) the equivalents of acetic anhydride are serially reduced to about 1 equivalent based on the loading of the solid support. In certain embodiments, the volume of the mixture of capping reagents is modified independently for each cycle of steps b) through e) such that about 8 equivalents of acetic anhydride are used for the first cycle and over each successive cycle that includes the capping step e) the equivalents of acetic anhydride are serially reduced to about 1 equivalent based on the loading of the solid support. In certain embodiments, the volume of the mixture of capping reagents is modified independently for each cycle of steps b) through e) such that about 4 equivalents of acetic anhydride are used for the first cycle and over each successive cycle that includes the capping step e) the equivalents of acetic anhydride are serially reduced to about 1 equivalent based on the loading of the solid support.

In certain embodiments, the mixture of capping reagents comprises from about 5% to about 10% acetic anhydride, from about 5% to about 10% N-methylimidazole and from about 5% to about 15% pyridine or from about 5% to about 10% 2,6-lutidine dissolved in tetrahydrofuran, toluene or acetonitrile. In certain embodiments, the mixture of capping reagents comprises from about 5% to about 10% acetic anhydride, from about 5% to about 10% N-methylimidazole and from about 5% to about 15% pyridine in toluene. In certain embodiments, the mixture of capping reagents comprises from about 10% acetic anhydride, about 10% N-methylimidazole and about 15% pyridine in toluene.

In certain embodiments, each iterative step e) is omitted.

In certain embodiments, the oligomeric compound comprises from about 10 to about 40 monomer subunits in length. In certain embodiments, the oligomeric compound comprises from about 12 to about 30 monomer subunits in length. In certain embodiments, the oligomeric compound comprises from about 14 to about 20 monomer subunits in length.

BRIEF DESCRIPTION OF THE FIGURES

FIG. 1 illustrates an overlay of the average mass spectra under main UV peaks for the comparison of Method B (no capping) to the control Method A (standard capping) for 5-10-5 MOE gapmer-1 on a 2.0 mmol scale (overlay of FIGS. 2 and 3).

FIG. 2 illustrates an average mass spectra under main UV peaks for 5-10-5 MOE gapmer-1 on a 2.0 mmol scale using Method A (standard capping).

FIG. 3 illustrates an average mass spectra under main UV peaks for 5-10-5 MOE gapmer-1 on a 2.0 mmol scale using Method B (no capping).

FIG. 4 illustrates an overlay of average mass spectra under main UV peaks for the comparison of Method C (½ capping) to the control Method A (standard capping) for 5-10-5 MOE gapmer-1 on a 550 mmol scale (overlay of FIGS. 5 and 6).

FIG. 5 illustrates an average mass spectra under main UV peaks for 5-10-5 MOE gapmer-1 on a 550 mmol scale using Method A (standard capping).

FIG. 6 illustrates an average mass spectra under main UV peaks for 5-10-5 MOE gapmer-1 on a 550 mmol scale using Method C (½ capping).

FIG. 7 illustrates an overlay of average mass spectra under main UV peaks for the comparison of Method B (no capping) to the control Method A (standard capping) for 5-10-5 MOE gapmer-2 on a 2.0 mmol scale (overlay of FIGS. 8 and 9).

FIG. 8 illustrates an average mass spectra under main UV peaks for 5-10-5 MOE gapmer-2 on a 2.0 mmol scale using Method A (standard capping).

FIG. 9 illustrates an average mass spectra under main UV peaks for 5-10-5 MOE gapmer-2 on a 2.0 mmol scale using Method B (no capping).

FIG. 10 illustrates an overlay of average mass spectra under main UV peaks for the comparison of Method D (no capping except for UnyLinker) to the control Method A (standard capping) for 5-10-5 MOE gapmer-3 on a 2.0 mmol scale (overlay of FIGS. 11 and 12), FIG. 11 illustrates an average mass spectra under main UV peaks for 5-10-5 MOE gapmer-3 on a 2.0 mmol scale using Method A (standard capping).

FIG. 12 illustrates an average mass spectra under main UV peaks for 5-10-5 MOE gapmer-3 on a 2.0 mmol scale using Method D (no capping except for Unylinker).

FIG. 13 illustrates an overlay of average mass spectra under main UV peaks for the comparison of Method B (no capping), Method C (½ capping) and Method E (¼ capping) to the control Method A (standard capping) for 5-10-5 MOE gapmer-4 on a 2.0 mmol scale (overlay of FIGS. 14, 15, 16 and 17).

FIG. 14 illustrates an average mass spectra under main UV peaks for 5-10-5 MOE gapmer-4 on a 2.0 mmol scale using Method A (standard capping).

FIG. 15 illustrates an average mass spectra under main UV peaks for 5-10-5 MOE gapmer-4 on a 2.0 mmol scale using Method B (no capping).

FIG. 16 illustrates an average mass spectra under main UV peaks for 5-10-5 MOE gapmer-4 on a 2.0 mmol scale using Method C (½ capping).

FIG. 17 illustrates an average mass spectra under main UV peaks for 5-10-5 MOE gapmer-4 on a 2.0 mmol scale using Method E (¼ capping).

DETAILED DESCRIPTION OF THE INVENTION

Overview

Oligomer synthesis can be performed using solution or solid phase chemistries. In solid phase oligonucleotide synthesis, oligonucleotides are assembled in a cyclical manner, each cycle consisting of a series of chemical reactions. Typically the first reaction is a deblocking reaction, i.e. the removal of a hydroxyl protecting group from a nucleoside monomer or an oligomer bound to a support. Generally, this requires the removal of a dimethoxytrityl protecting group to provide a free hydroxyl group. The next reaction is a coupling reaction, normally performed in the presence of an activator, wherein the free hydroxyl group is reacted with a nucleoside phosphoramidite to provide a phosphite triester. The next reaction is the oxidation or sulfurization of the phosphite triester to a phosphate triester or thiophosphate triester. The next reaction is the acetylation of unreacted free hydroxyl groups that failed to react with a phosphoramidite during the coupling cycle. This next step is referred to as the capping step and is performed using a mixture of capping reagents. Capping after the first phosphoramidite has been coupled is also effective in capping free hydroxyl and/or amino groups remaining on the solid support and free hydroxyl groups remaining on universal linker groups.

In certain instances, coupling of free the hydroxyl group with phosphoramidites out of sequence results in synthesis failure. In certain such instances, a hydroxyl group is deblocked but fails to couple with the next phosphoramidite. The hydroxyl group may react in the next and subsequent cycles, but will still lack the nucleoside that should have been added at the failed coupling reaction. The resulting oligonucleotide will be shorter than the desired length. Resulting oligonucleotides are described by the number of nucleosides absent from the desired length as "n minus [x]" where [x] is the number of missing nucleosides. Thus, an oligonucleotide in which a single coupling reaction fails is described as "n minus 1" or "n−1". Removal of n−1 oligonucleotides from the final product is difficult. A capping step was developed (see Beaucage et al., *Tetrahedron, Tetrahedron Report Number 309*, 1992, 48, 2291) wherein free hydroxyl groups that fail to couple are acetylated. Such acetylated or capped hydroxyl groups are unavailable for further reaction during the remainder of the iterative cycles. Thus, if a single coupling reaction fails, the oligonucleotide is prevented from coupling in subsequent cycles, resulting in a failed product having n minus >1. Such shorter failed products are more easily removed from the final product than n minus 1 oligonucleotides.

Various reagents have been used in the capping step of oligonucleotide synthesis (e.g., Capping Reagent A and Capping Reagent B, DMAP NMI (see Eadie et al., *Nucleic Acids Research*, 1987, 15(20), 8333-8349), In certain instances, oligonucleotides such as those synthesized by Eadie in the 1980s and later may be synthesized on Applied Biosciences automated DNA synthesizers, such as the ABI 380A and ABI 381A following standard protocols provided with the synthesizers. The program for the ABI 392/394 DNA/RNA synthesizers dated May 1, 1991, instruct using 190 μL of equal volumes of Cap A and Cap B for each capping reaction (Cap A: 10% acetic anhydride and 10% 2,6-lutidine in THF; Cap B: and 16% NMI in THF, 1 μmol scale). Thus, these automated ABI synthesizers (at least the ABI 392/294) teach performing the capping steps using 9.5 equivalents of acetic anhydride based on the loading of the solid support.

In certain embodiments, mixture of capping reagents having 10% by volume of acetic anhydride and delivering about 17 equivalents for each capping step (600 mmol loading) may be used. In certain embodiments, a universal linking group may be used. Certain such universal linking groups require coupling of the first phosphoramidite followed by oxidation or sulfurization and a capping step. In certain embodiments, coupling a 3'-succinyl functionalized nucleoside to a solid support would not require oxidation or sulfurization but may require a capping step. In certain instances, a larger excess of acetic anhydride for this first capping step is provided when a universal linking group is used (e.g., about 85 equivalents when using Unylinker™ functionalized solid support). As used herein the "equivalents of acetic anhydride" present in a given volume of a mixture of capping reagents is calculated based on the moles of acetic anhydride in the mixture divided by the molar scale of the overall synthesis.

There has been a trend over the years to maintain or increase the equivalents of acetic anhydride used for capping steps in solid phase oligonucleotide synthesis. The purity and yield of synthetic oligonucleotides has been steadily increasing over this same period due to other improvements in the overall process. Currently, automated solid phase oligonucleotide synthesis is used to prepare drugs on multi-kilo scales. In certain instances, GMP quality, large scale automated synthesis of oligonucleotides is routinely being performed on scales as large as 600 mmol, providing about 4.5 g per mmol (~2.7 kg/600 mmol run). In certain embodiments, the present invention is suitable for synthesis at such scale.

In certain instances, mixtures of capping reagents providing large molar excesses of acetic anhydride can reduce the over yield and purity for automated solid phase synthesis of oligonucleotides. In certain embodiments, the present invention provides improved protocols for the capping step during the synthesis of oligonucleotides and oligomeric compounds in general.

Provided herein are improved methods for the synthesis of oligomeric compounds. The current standard for the synthesis of oligonucleotides is the phosphoramidite method utilizing phosphoramidites in an iterative process of coupling nucleoside phosphoramidites to 5'-hydroxyl groups of nucleoside monomers or growing oligomers that are attached to a solid support. This current standard method is also used to prepare oligomeric compounds wherein one or more of the nucleoside phosphoramidites is modified.

During the typical synthesis of oligomeric compounds, one of the steps that is performed for each iterative cycle except the last one is the capping step. The capping step is typically performed following the oxidation or sulfurization step and is omitted in the last cycle after the last phosphoramidite has been coupled. The capping step is performed by treating the solid support with a mixture of capping reagents. The mixture of capping reagents is generally an equal volume of two solutions that are mixed at the time of use. The industry has generally labeled these two solutions Capping Reagent A and Capping Reagent B. Generally, one of Capping Reagent A and Capping Reagent B comprises acetic anhydride in a suitable solvent and the other of Capping Reagent A and Capping Reagent B comprises an organic base in a suitable solvent. A further reagent is included in one of the solutions to assist the acetylation reaction such as N-methylimidazole.

In certain embodiments, one of Capping Reagent A and Capping Reagent B comprises acetic anhydride in an appropriate solvent and the other of Capping Reagent A and Capping Reagent B comprises is N-methylimidazole and an organic base in an appropriate solvent. The mixture of capping reagents rapidly acetylates free hydroxyl groups by reaction with acetic anhydride assisted by NMI. The organic base maintains a basic pH to prevent detritylation of the DMT protected hydroxyl group on the last phosphoramidite to be coupled to the growing oligomer. Examples of mixtures of capping reagents include: 10% acetic anhydride and 10% 2,6-lutidine in THF mixed with equal volume of 16% N-methylimidazole (NMI) in THF (1991 ABI); 20% acetic anhydride in toluene mixed with equal volume of 30% pyridine and 20% NMI in toluene (current large scale in house); 10% acetic anhydride and 10% pyridine in THF mixed with an equal volume of 17.6% w/v NMI in acetonitrile (atdbio) wherein the percentages are in v/v. In certain embodiments, the mixture of capping reagents is 10% acetic anhydride, 15% pyridine and 10% NMI in toluene.

The iterative capping steps described herein pertain to the capping step that is optionally performed after a second monomer subunit has been coupled to a first monomer subunit that is attached to a solid support wherein each monomer subunit is a nucleoside or modified nucleoside. The capping step is then optionally performed after each successive iterative cycle wherein addition monomer subunits are added. There is no capping step performed after the addition of the last monomer subunit. The equivalents of acetic anhydride used for capping at each step is calculated by dividing the number of moles of acetic anhydride used by the loading of the solid support (17.2 equivalents of acetic anhydride are delivered for a particular capping step when the volume of the mixture of capping reagents provides 10.3 moles of acetic anhydride and the loading of the solid support is 600 mmol, 10.3/0.6=17.2 eq.).

The loading of the solid support is typically calculated by trityl analysis. A small quantity of the solid support (~1 mg) is treated with a strong acid (e.g. a 1:1 mixture of concentrated HCl/EtOH) to cleave the DMT group. The absorbance at 495 nm of a sample of the resulting orange solution is measured in a UV/visible spectrophotometer. The amount of DMT cation is then calculated (extinction coefficient of DMT cation @ 495 nm, $E_{495}$=71,700$M^{-1}$ $cm^{-1}$; Loading (1 mg solid support)=($E_{495}/A_{495} \times V \times (1/f)$).

Solid supports can be purchased with a first monomer subunit attached thereto wherein the linkage between the monomer subunit and the solid support is an ester type linkage such as a succinyl linkage. These functionalized solid supports are commercially available with a variety of nucleosides and linkages and are ready for automated synthesis without further treatment.

In certain embodiments, the solid support is functionalized with a universal linking group such as the Unylinker™ group. When a universal linking moiety such as the Unylinker™ group is used the first monomer subunit is coupled the Unylinker™ group thereby providing a phosphite triester linkage to the Unylinker™ group. The linkage is then oxidized to the phosphate triester or sulfurized to the thiophosphate triester. Any unreacted free hydroxyl groups on the Unylinker™ groups are then capped. This capping step is not part of the iterative capping steps described herein in that it uses a larger number of equivalents relative to the other iterative capping steps and isn't between two monomer subunits. Hence the capping of the universal linking group after addition of the first monomer subunit is separate from the iterative cycles or iterative capping steps.

Provided herein are methods for preparing oligomeric compounds wherein the iterative capping step has been modified or eliminated at one or more iterative cycles during solid phase oligonucleotide synthesis. In certain embodiments, the capping step is eliminated at each iterative cycle. In certain embodiments, the capping step is performed for about the first 25% of the iterative cycles and omitted for about the remaining 75% of the iterative cycles. In certain embodiments, the capping step is performed for about the first 50% of the iterative cycles and omitted for about the remaining 50% of the iterative cycles. In certain embodiments, the capping step is performed for about the first 75% of the iterative cycles and omitted for about the remaining 25% of the iterative cycles.

In certain embodiments, the volume of the mixture of capping reagents is adjusted such that only about 8 equivalents of acetic anhydride is used for each of the iterative capping steps that are performed. In certain embodiments, the volume of the mixture of capping reagents is adjusted such that only about 6 equivalents of acetic anhydride is used for each of the iterative capping steps that are performed. In certain embodiments, the volume of the mixture of capping reagents is adjusted such that only about 4 equivalents of acetic anhydride is used for each of the iterative capping steps that are performed. In certain embodiments, the volume of the mixture of capping reagents is adjusted such that only about 2 equivalents of acetic anhydride is used for each of the iterative capping steps that are performed. In certain embodiments, the volume of the mixture of capping reagents is adjusted such that less than about 1 equivalents of acetic anhydride is used for each of the iterative capping steps that are performed.

In certain embodiments, the volume of the mixture of capping reagents is modified independently for each iterative cycle of steps b) through e) such that about 17 equivalents of acetic anhydride are used for the first iterative cycle and over each successive iterative cycle that includes the capping step e) the equivalents of acetic anhydride are serially reduced to about 1 equivalent based on the loading of the solid support. In certain embodiments, the serial reduction of the equivalents of acetic anhydride from about 17 equivalents to about 1 equivalent is applied to each iterative cycle except the last. In certain embodiments, the serial reduction of the equivalents of acetic anhydride from about 17 equivalents to about 1 equivalent is applied to only about the first 75% of the iterative cycles and the capping step is omitted for the remaining iterative cycles. In certain embodiments, the serial reduction of the equivalents of acetic anhydride from about 17 equivalents to about 1 equivalent is applied to only about the first 50% of the iterative cycles and the capping step is omitted for the remaining iterative cycles. In certain embodiments, the serial reduction of the equivalents of acetic anhydride from about 17 equivalents to about 1 equivalent is applied to only about the first 25% of the iterative cycles and the capping step is omitted for the remaining iterative cycles.

In certain embodiments, the volume of the mixture of capping reagents is modified independently for each iterative cycle of steps b) through e) such that about 8 equivalents of acetic anhydride are used for the first iterative cycle and over each successive cycle that includes the capping step e) the equivalents of acetic anhydride are serially reduced to about 1 equivalent based on the loading of the solid support. In certain embodiments, the serial reduction of the equivalents of acetic anhydride from about 8 equivalents to about 1 equivalent is applied to each iterative cycle except the last. In certain embodiments, the serial reduction of the equivalents of acetic anhydride from about 8 equivalents to about 1 equivalent is applied to only about the first 75% of the iterative cycles and the capping step is omitted for the remaining iterative cycles. In certain embodiments, the serial reduction of the equivalents of acetic anhydride from about 8 equivalents to about 1 equivalent is applied to only about the first 50% of the iterative cycles and the capping step is omitted for the remaining iterative cycles. In certain embodiments, the serial reduction of the equivalents of acetic anhydride from about 8 equivalents to about 1 equivalent is applied to only about the first 25% of the iterative cycles and the capping step is omitted for the remaining iterative cycles.

In certain embodiments, the volume of the mixture of capping reagents is modified independently for each iterative cycle of steps b) through e) such that about 4 equivalents of acetic anhydride are used for the first iterative cycle and over each successive cycle that includes the capping step e) the equivalents of acetic anhydride are serially reduced to about 1 equivalent based on the loading of the solid support. In certain embodiments, the serial reduction of the equivalents of acetic anhydride from about 4 equivalents to about 1 equivalent is applied to each iterative cycle except the last. In certain embodiments, the serial reduction of the equivalents of acetic anhydride from about 4 equivalents to about 1 equivalent is applied to only about the first 75% of the iterative cycles and the capping step is omitted for the remaining iterative cycles. In certain embodiments, the serial reduction of the equivalents of acetic anhydride from about 4 equivalents to about 1 equivalent is applied to only about the first 50% of the iterative cycles and the capping step is omitted for the remaining iterative cycles. In certain embodiments, the serial reduction of the equivalents of acetic anhydride from about 4 equivalents to about 1 equivalent is applied to only about the first 25% of the iterative cycles and the capping step is omitted for the remaining iterative cycles.

The present methods are applicable to the preparation of oligomeric compounds comprising a wide range of monomer subunits such as nucleosides and modified nucleosides. In general each of the monomer subunits comprises a protected hydroxyl group and a phosphoramidite group. In certain embodiments, the hydroxyl protecting group is selected from substituted or unsubstituted trityl groups. In certain embodiments, the hydroxyl protecting group is 4,4'-dimethoxytrityl (DMT). In certain embodiments, the phosphoramidite group has the formula $-P(NR_2R_3)(OR_4)$, wherein $R_2$ and $R_3$ are each, independently, $C_1$-$C_6$ straight or branched alkyl, which includes but is not limited to, methyl, ethyl, n-propyl, 2-propyl, n-butyl, iso-butyl, and similar alkyl groups, and $R_4$ is any group that is compatible with oligonucleotide synthesis that may be removed after synthesis is complete. Preferably, $R_4$ is a substituted $C_1$-$C_6$ alkyl including at least one heteroatom. Most preferably, $R_4$ is $-CH_2CH_2CN$. A preferred phosphoramidite group is diisopropylcyanoethoxy phosphoramidite ($-P(N[(CH)CH_3]_2)(O(CH_2)_2CN)$).

In certain embodiments, methods of synthesizing of oligomeric compounds are provided that utilize support medium. In certain embodiments, reactive groups on the support medium are first functionalized with Unylinker™ linking groups prior to addition of the first monomer subunit. A first monomer subunit is attached to a support medium with subsequent monomer subunits iteratively coupled to provide a desired oligomeric compound. The industry standard for large scale oligomeric compound synthesis uses solid support media in a reaction vessel. The growing oligomeric compound is reacted and washed with various reagents and solvents while attached to the solid support. In certain embodiments, support media can be selected having variable solubility in different solvents to allow the growing support bound oligomeric compound to be either in or out of solution at various points in the synthesis process as desired. In certain embodiments, soluble supports include soluble polymer supports that allow precipitating and dissolving the iteratively synthesized product at desired points in the synthesis (Gravert et al., Chem. Rev., 1997, 97, 489-510).

The term "support media" is intended to include all forms of support, including those known to the art skilled for the synthesis of oligomeric compounds. Some representative support media that are amenable to the methods of the present invention include but are not limited to the following: crosslinked polystyrene (Primer Support 5G or NittoPhaseHL), controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloyl-ethylenediamine, including a known amount of N-tertbutoxy-carbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin I 538 (1981)).

Further support media amenable to the present invention include without limitation a composite of a resin and another material that is also substantially inert to the organic synthesis reaction conditions employed. One exemplary composite (see Scott, et al., J. Chrom. Sci., 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, Israel J. Chem. 1978, 17, 243 and van Rietschoten in Peptides 1974, Y. Wolman, Ed., Wiley and Sons, New York, 1975, pp. 113-116). Contiguous solid supports other than PEPS, such as cotton sheets (Lebl and Eichler, Peptide Res. 1989, 2, 232) and hydroxypropylacrylate-coated polypropylene membranes (Daniels, et al., Tetrahedron Lett. 1989, 4345). Acrylic acid-grafted polyethylene-rods and 96-microtiter wells to immobilize the growing peptide chains and to perform the compartmentalized synthesis. (Geysen, et al., Proc. Natl. Acad. Sci. USA, 1984, 81, 3998). A "tea bag" containing traditionally-used polymer beads. (Houghten, Proc. Natl. Acad. Sci. USA, 1985, 82, 5131). Simultaneous use of two different supports with different densities (Tregear, Chemistry and Biology of Peptides, J. Meienhofer, ed., Ann Arbor Sci. Publ., Ann Arbor, 1972 pp. 175-178). Combining of reaction vessels via a manifold (Gorman, Anal. Biochem., 1984, 136, 397). Multicolumn solid-phase synthesis (e.g., Krchnak, et al., Int. J. Peptide Protein Res., 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., Collect. Czech. Chem. Commun, 1989, 54, 1746). Support mediated synthesis of peptides have also been reported (see, Synthetic Peptides: A User's Guide, Gregory A. Grant, Ed. Oxford University Press 1992; U.S. Pat. Nos. 4,415,732; 4,458,066; 4,500,707; 4,668, 777; 4,973,679; 5,132,418; 4,725,677 and Re-34,069.)

The present methods can be used to prepare oligomeric compounds comprising a particular motif. As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound. Such motifs include without limitation, gapmer motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include terminal groups at one or both of the 5' and or 3' terminals such as a conjugate or reporter group.

The preparation of motifs has been disclosed in various publications including without limitation, representative U.S. Pat. Nos. 5,013,830; 5,149,797; 5,220,007; 5,256,775; 5,366, 878; 5,403,711; 5,491,133; 5,565,350; 5,623,065; 5,652,355; 5,652,356; and 5,700,922; and published international applications WO 2005/121371 and WO 2005/121372 (both published on Dec. 22, 2005), certain of which are commonly owned with the instant application, and each of which is herein incorporated by reference in its entirety.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxyl)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin -4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or logP, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein the terms "nucleobase" and "heterocyclic base moiety" refer to unmodified or naturally occurring nucleobases as well as modified or non-naturally occurring nucleobases and synthetic mimetics thereof (such as for example phenoxazines). In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methylcytosine, 6-N-benzoyladenine or 2-N-isobutyrylguanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S.: 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2',5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH($CH_3$)-4', 2'-O—$CH_2$-4' or 2'-O—($CH_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the terms "sugar substituent group" or more generally "substituent group" refer to groups that are covalently attached to sugar moieties. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'- OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$—SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'- OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted $C_1$-$C_{10}$ alkyl or a protecting group and where n and m are from 1 to about 10.

In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)] wherein each R$_m$ and R$_n$ is, independently, H, substituted or unsubstituted $C_1$-$C_{10}$ alkyl or a protecting group. In certain embodiments, examples of 2,-sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR$_1$)[N(R$_1$)(R$_2$)] wherein R$_1$ and R$_2$ are each independently, H or $C_1$-$C_2$ alkyl. In certain embodiments, examples of sugar substituent groups include without limitation fluoro, —O—CH$_3$, —O—CH$_2$)$_2$—O—CH$_3$, —O—CH$_2$C(=O)—N(H)(CH$_3$), —O—CH$_2$C(=O)—N(H)—(CH$_2$)$_2$—N(CH$_2$)$_2$—N(CH$_2$) and —O—CH$_2$—N(H)—C(=NCH$_3$)[N(CH$_3$)$_2$]. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$) and —O—CH$_2$C(=O)—N(H)—(CH$_2$)$_2$—N(CH$_3$)$_2$. Further examples of modified sugar moieties include without limitation bicyclic sugars (e.g. bicyclic nucleic acids or bicyclic nucleosides discussed below).

In certain embodiments, examples of "sugar substituent group" or more generally "substituent group" include without limitation one or two 5'-sugar substituent groups independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with more than one sugar substituent group including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the term "monomer subunit" is meant to include all manner of monomer subunits that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides.

As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2',3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose or modified furanose sugar group such as a 4'-S analog. Modified furanose ring systems include 4'-S analogs, one or more substitutions at any position such as for example the 2', 3', 4' and 5' positions and addition of at least one bridge to form a polycyclic ring system such as a bicyclic system wherein a 2'-O—CH(CH$_3$)-4' bridge is added. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO2008/150729, published Dec. 11, 2008); 4'-CH$_2$—O—N(CH$_3$)-2' (see U.S. Pat. No. 7,96,345, issued on Apr. 13, 2010); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A., 2000, 97, 5633-5638; Singh et al., Chem. Commun, 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication No. US2008-0039618; U.S. Patent Application Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C($R_a$)($R_b$)]$_n$—, —[C($R_a$)($R_b$)]$_n$—O—, —C($R_a R_b$)—N(R)—O— or —C($R_a R_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

In certain embodiments, bicyclic nucleosides have the formula:

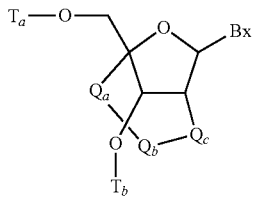

wherein:
Bx is a heterocyclic base moiety;
-$Q_a$-$Q_b$-$Q_c$- is —CH$_2$—N($R_c$)—CH$_2$—, —C(=O)—N($R_c$)—CH$_2$—, —CH$_2$—O—N($R_c$)—, —CH$_2$—N($R_c$)—O— or —N($R_c$)—O—CH$_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

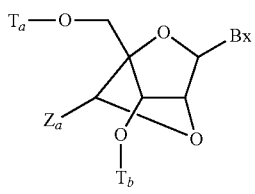

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, O$J_c$, N$J_c J_d$, S$J_c$, N$_3$, OC(=X)$J_c$, and N$J_e$C(=X)N$J_c J_d$, wherein each $J_c$, $J_d$ and $J_e$ is, independently, H, $C_1$-$C_6$ alkyl, or substituted $C_1$-$C_6$ alkyl and X is O or N$J_c$.

In certain embodiments, bicyclic nucleosides have the formula:

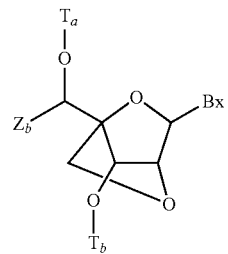

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

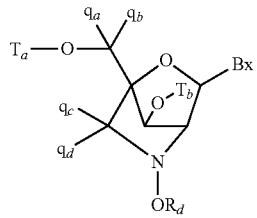

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

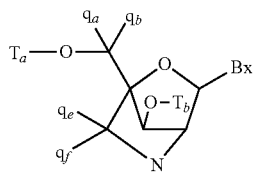

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

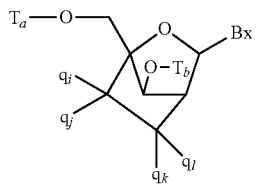

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy) (4'-$CH(CH_3)$—O-2') BNA (also referred to as constrained ethyl or cEt), (G) methylenethio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA, and (K) vinyl BNA as depicted below.

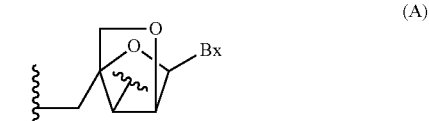

(A)

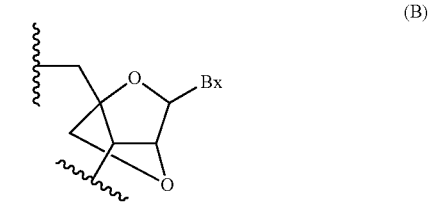

(B)

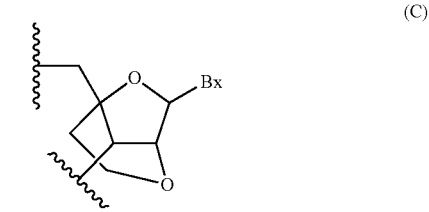

(C)

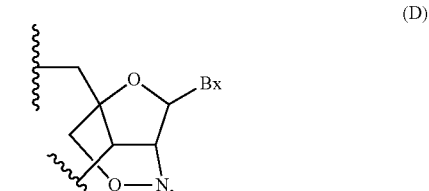

(D)

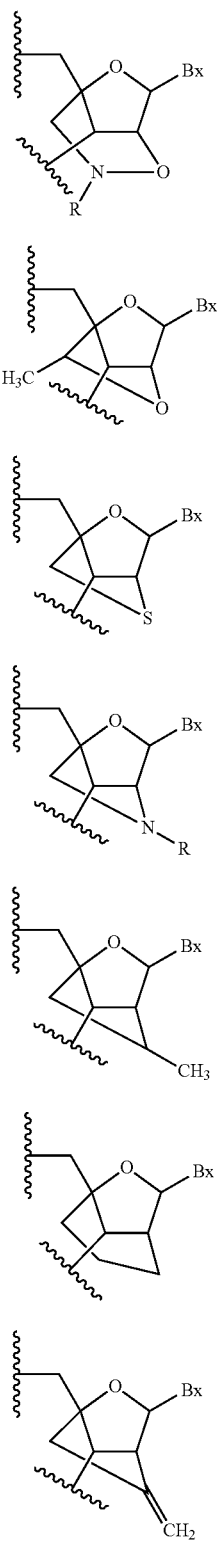

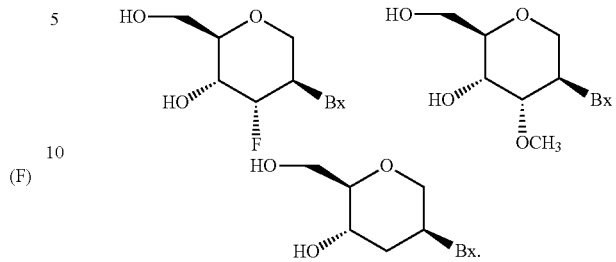

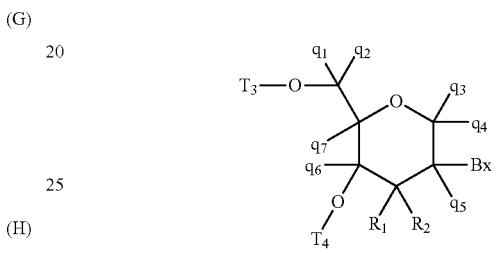

wherein Bx is the base moiety and R is, independently, H, a protecting group, $C_1$-$C_6$ alkyl or $C_1$-$C_6$ alkoxy.

In certain embodiments, modified nucleosides include nucleosides having sugar surrogate groups that include without limitation, replacement of the ribosyl ring with a sugar surrogate such as a tetrahydropyranyl ring system (also referred to as hexitol) as illustrated below:

In certain embodiments, sugar surrogates are selected having the formula:

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is P, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica*, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

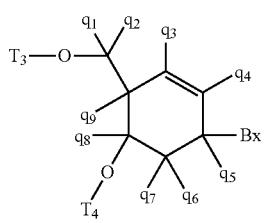

wherein independently for each of the at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

Some representative U.S. patents that teach the preparation of such modified sugars include without limitation, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

The modified nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and CH$_2$ component parts.

As used herein, the term "oligomeric compound" refers to a contiguous sequence of linked monomer subunits. Each linked monomer subunit normally includes a heterocyclic base moiety but monomer subunits also include those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleoside mimetics and or nucleosides having sugar surrogate groups.

In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-CH$_2$—C(=O)—N(H)-5'), amide-4 (3'-CH$_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos.: 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative U.S. patents that teach the preparation of the above oligonucleosides include without limitation, U.S. Pat Nos.: 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are nonionic. Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxoctanoic acid (ADO), succinimidyl 4-(N-maleimidomethyl) cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

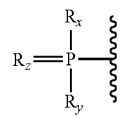

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$ wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA: Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Amen Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl] . In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

Those skilled in the art, having possession of the present disclosure will be able to prepare oligomeric compounds, comprising a contiguous sequence of linked monomer subunits, of essentially any viable length. While in certain embodiments, oligomeric compounds provided herein can be prepared as described, the following examples serve only to illustrate and are not intended to be limiting.

EXAMPLE 1

Unylinker™ Functionalized Support Medium

Solid support material, Primer Support 5G or NittoPhase-HL, functionalized with universal linking groups (Unylinker™) is commercially available from H.C. Brown Pharmaceutical Research and Laboratories. Unylinker™ and macroporous aminomethyl resin are also commercially available separately from Tianjin Nankai Hecheng Science and Technology Company, Ltd.

EXAMPLE 2

Preparation of Solutions Used for the Synthesis of Oligomeric Compounds

Unless otherwise stated, solvents have water content less than 100 ppm as determined by Karl Fischer titrimetry. The concentrations of reagents listed herein and the solvents utilized are typical and not meant to be limiting.

The detritylation solution is typically prepared in a 1:9 volumetric ratio of dichloroacetic acid (DCA) to toluene. The volumetric ratio of DCA to toluene can also be varied. The detritylation solution is prepared in the lab or special ordered from either Tedia or EMD Chemicals. The detritylation solution is used in the detritylation step "B" for deprotecting the 4,4'-Dimethoxytrityl (5'-DMT) groups.

The 0.2 M amidite solutions are typically prepared in the lab by adding the solid amidite directly into an appropriately filled dedicated reservoir with acetonitrile (ACN). The activator solution is typically prepared in the lab by adding the solid 4,5-dicyanoimidazole (DCI) and liquid N-methylimidazole (NMI) directly into an appropriate filled reservoir with acetonitrile mixture to have a final concentration of 1.0 M DCI and 0.1 M NMI. The concentrations of phosphoramidite, DCI and NMI can also be varied. The selected phosphoramidite solution is automatically mixed with the activator solution in a 1:1 volumetric ratio by an automated synthesizer to create the coupling solution. The coupling solution is used in the coupling step "D" to add 5'-DMT phosphoramidite monomer subunits.

Typical phosphoramidite solutions include without limitation: 5'-DMT-2'-deoxyadenosine phosphoramidite (0.2 M, dA amidite); 5'-DMT-2'-deoxycytosine phosphoramidite (0.2 M, dC amidite), 5'-DMT-2'-deoxy-5-methylcytosine phosphoramidite (0.2 M, $d^{Me}C$ amidite), 5'-DMT-2'-deoxyguanosine phosphoramidite (0.2 M, dG amidite), 5'-DMT-2'-deoxythymidine phosphoramidite (0.2 M, dT amidite), 5'-DMT-2'-O(CH$_2$)$_2$—OCH$_3$ adenosine phosphoramidite (0.2 M, 2'-MOE A amidite); 5'-DMT-2'-O(CH$_2$)$_2$—OCH$_3$ 5-methylcytosine phosphoramidite (0.2 M, 2'-MOE $^{Me}C$ amidite); 5'-DMT-2'-O(CH$_2$)$_2$—OCH$_3$ guanosine phosphoramidite (0.2 M, 2'-MOE G amidite) and 5'-DMT-2'-O(CH$_2$)$_2$—OCH$_3$ 5-methyluridine phosphoramidite (0.2 M, 2'-MOE $^{Me}U$ amidite), 5'-DMT-2',4'-O(CHCH$_3$) adenosine phosphoramidite (0.2 M, 2',4'-cEt A amidite), 5'-DMT-2',4'-O(CHCH$_3$) 5-methylcytosine phosphoramidite (0.2 M, 2',4'-cEt $^{Me}C$ amidite); 5'-DMT-2',4'-O(CHCH$_3$)-guanosine phosphoramidite (0.2 M, 2',4' cEt G amidite) and 5'-DMT-2',4'-O (CHCH$_3$) 5-methyluridine phosphoramidite (0.2 M, 2',4'-cEt $^{Me}U$ amidite).

The 0.2 M phenylacetyl disulfide (PADS) sulfurization solution is typically prepared in the lab by adding the solid reagent directly to an appropriate reservoir filled with equal volumes of acetonitrile and 3-picoline (3-PIC). The concentration of PADS and volumetric ration of ACN to 3-PIC can also be varied. Once the PADS solution is completely mixed it is then allowed to age 12 hours prior to use in the synthesis sulfurization step "F".

The solutions used for capping are Capping Reagent A (2/3/5 volumetric mix of N-methylimidazole/pyridine/toluene) and Capping Reagent B (1/4 volumetric mix of acetic anhydride in toluene). The volumetric ratio of NMI, pyridine and toluene for Capping Reagent A and the volumetric ratio of acetic anhydride and toluene for Capping Reagent B can also be varied. Capping Reagent A and Capping Reagent B are prepared in the lab or special ordered from either Tedia or EMD Chemicals. A solution of Capping Reagent A is automatically mixed with a solution of Capping Reagent B in a 1:1 volumetric ratio by an automated synthesizer to create the capping solution (mixture of capping reagents). The capping solution is used in the capping step "H" for capping (acetylation) of any uncoupled free hydroxyl groups due to incomplete coupling.

The phosphorus deprotection solution is typically prepared in a 1:1 volumetric ratio of triethylamine/acetonitrile. The phosphorus deprotection solution is typically prepared in the lab. The volumetric ratio of triethylamine and ACN can also be varied. The phosphorus deprotection solution is used in the phosphorus deprotection step "J" for deprotecting the phosphorus protecting groups.

| Synthesis Step | Synthesis Solution | Reagent/Solvent |
|---|---|---|
| A | Column Packing | Primer Support 5G or NittoPhase-HL solid support slurried in Acetonitrile |
| B | Detritylation | Dichloroacetic Acid/Toluene (1:9, v/v) |
| C | Detritylation Rinse | Toluene or Acetonitrile |
| D | Coupling | 0.2M Phosphoramidite in Acetonitrile |
|   | Coupling Activator | 1.0M 4,5-Dicyanoimidazole with 0.1M N-methylimidazole in Acetonitrile |
| E | Coupling Rinse | Acetonitrile |
| F | Sulfurization | 0.2M Phenylacetyl Disulfide in Acetonitrile/3-Picoline (1:1, v/v) aged ≥12 hours |
| G | Sulfurization Rinse | Acetonitrile |
| H | Capping A | N-methylimidazole/Pyridine/Toluene (2:3:5, v/v/v) |
|   | Capping B | Acetic Anhydride/Toluene (1:4, v/v) |
| I | Capping Rinse | Toluene or Acetonitrile |
| J | Phosphorus Deprotection | Triethylamine/Acetonitrile (1:1, v/v) |
| K | End Wash | Toluene or Acetonitrile. |

EXAMPLE 3

Calculation of Capping Equivalents (Equivalents of Acetic Anhydride) for Capping Step "H"

The capping equivalent for each step is defined as the molar ratio of acetic anhydride delivered for that step to the solid support loading (moles acetic acid/moles of Unylinker™ or first monomer loaded onto support). The capping equivalent is controlled by the synthesizer programming to increase or decrease the total capping volume delivered to the synthesis column. For example when the loading of the solid support has been determined at 600 mmol and 10.3 moles of acetic anhydride are delivered in the mixture of capping reagents then a total of 17.2 equivalents of acetic anhydride are delivered.

EXAMPLE 4

General Method for Preparing Oligomeric Compounds

The methods for preparing oligomeric compounds using solid phase is well known in the art and is outlined below:

A) In a synthesis column, slurry an appropriate solid support (solid phase), which the hydroxyl groups are protected with 4,4'-Dimethoxytrityl, in an appropriate solvent and pack to the desired packing density;

B) Deliver the detritylation solution to the solid support to remove the 4,4'-Dimethoxytrityl protecting group to expose the hydroxyl groups;

C) Wash the solid phase with one or more column volumes of one or more solvents and or mixtures of solvents;

D) Deliver the coupling solution with the appropriate nucleotide monomer subunit capable of forming phosphite intermediates with the free hydroxyl groups and activator solution in equal volumes to the solid support. As the solution exits the column, a recirculation loop allows the solution to contact the solid support one or more times;

E) Wash the solid phase one or more times with one or more solvents and or mixtures of solvents;

F) Deliver an oxidizing or sulfurizing solution to the solid support;

G) Wash the solid phase one or more times with one or more solvents and or mixtures of solvents;

H) Deliver the capping solutions in equal volumes to the solid support to cap any remaining uncoupled support-bound 5'-hydroxyl byproduct for a given cycle;

I) Wash the solid phase one or more times with one or more solvents and or mixtures of solvents and repeat step "B" through "I" one or more times to add one or more additional monomer subunits;

J) Deliver the phosphorus deprotecting solution to the solid phase to remove the phosphorus protecting groups;

K) Wash the solid phase one or more times with one or more solvents and or mixtures of solvents;

L) Deliver a cleaving solution to the solid phase capable of removing base protecting groups and cleaving the resultant oligomeric compound from the solid phase to provide the free oligomeric compound;

M) Isolate the free oligomeric compound from the solid phase through filtration;

N) Optionally, concentrate the crude oligomeric compound in vacuo;

O) Optionally, purify the oligomeric compound;

P) Repeat step "B" to remove the final hydroxyl protecting group; and

Q) Optionally, purify the oligomeric compound.

EXAMPLE 5

Modified Method for Preparing Oligomeric Compounds by Reducing or Eliminating Capping Step "H"

The capping step in standard solid-phase oligonucleotide synthesis is designed to prevent elongation of the free hydroxyl reaction sites left un-coupled for a given cycle. In the event of a significant coupling failure, the capping reaction allows for crude material of acceptable purity to be recovered.

Although capping provides the advantages as mentioned above, it is shown here that the capping reaction has a negative impact on the overall yield as well as the purity profile of the desired oligonucleotide following typical coupling protocols. To address this issue, automated solid phase oligonucleotide syntheses are performed using modified capping protocols as provided in the following examples.

Steps "A" through "G" and "I" through "P" were performed in the same manner as described in Example 4. Capping step "H" was modified by delivering a volume of capping reagents providing reduced equivalents of acetic anhydride to solid support to cap any remaining uncoupled 5'-hydroxyl groups for a given cycle or by eliminating capping step "H" entirely throughout the oligonucleotide synthesis.

EXAMPLE 6

Preparation of 5-10-5 MOE Gapmer-1 Using Standard Capping Protocol for Capping Step "H" (Method A)

Synthesis of 5-10-5 MOE gapmer-1 was performed on an ÄKTA OligoPilot 100 synthesizer at a 2.0 mmol scale using the procedures set forth below. The synthesis was performed using the general oligonucleotide synthetic method with the standard capping protocol (Method A). The MOE gapmer comprises five 2'-O—$(CH_2)_2$—$OCH_3$ (MOE) modified nucleosides on each of the 3' and 5' ends of the oligomeric compound and a ten 2'-deoxyribonucleosides in the gap wherein all of the internucleoside linkages are phosphorothioate internucleoside linkages.

Unylinker™ functionalized Primer Support 5G solid support (6.08 g solid support with 2.0 mmol of Unylinker™ loaded; 2.0 mmol loading) was weighed into the synthesis column and slurried in acetonitrile. The piston was lowered to the calculated bed height based on a 9.6 mL/g packing density. The column locking mechanisms were secured and connected to the synthesizer.

The appropriate reservoirs were charged with detritylation solution, phosphoramidite solutions, activator solution, sulfurization solution, capping solution A, capping solution B, phosphorus-deprotection solution, acetonitrile and toluene.

The support-bound Unylinker™ was swelled with toluene and immediately treated with the detritylation solution containing 10% DCA in toluene to provide free hydroxyl groups by removing the DMT protecting groups. After detritylation, the solid support was washed with acetonitrile twice.

The solid support was treated with a coupling solution having a total of 1.75 equivalents of phosphoramidite per coupling. The selected phosphoramidite solution is automatically mixed with the activator solution in a 1:1 volumetric ratio by the automated synthesizer before entering the synthesis column. The exiting coupling solution was then recycled through the solid phase via a recirculation loop to ensure sufficient time for the incorporation of the phosphoramidite monomer subunit. After coupling recirculation, the solid phase was washed with acetonitrile.

The solid phase was then treated with an aged PADS solution containing 0.2 M PADS in acetonitrile/3-picoline to convert phosphite triester internucleoside linkages into thiophosphate triester internucleoside linkages. After sulfurization, the solid phase was washed with acetonitrile.

The solid phase was then treated with a capping solution having a total of 86 equivalents of acetic anhydride for the first cycle and 17 equivalents of acetic anhydride for each subsequent coupling except for the final cycle. Capping reagent A is automatically mixed with the capping reagent B in a 1:1 volumetric ratio by the automated synthesizer before entering the synthesis column. The exiting capping solution was then recycled through the solid phase via a recirculation loop only for the first synthesis cycle to ensure acetylation capping of any unreacted hydroxyl groups. After capping, the solid phase was washed with toluene. The iterative cycle was repeated 19 times to prepare the 5-10-5 MOE gapmer on the solid support.

The support-bound DMT-on oligomeric compound was treated with a phosphorus deprotection solution containing a 1:1 volumetric ration of TEA and acetonitrile. The phosphorus deprotection solution was recycled through the solid phase via a recirculation loop to ensure sufficient time to remove the CNET protecting groups. After this deprotection the solid phase was washed with toluene.

The solid support was removed from the column and dried per established procedures. The support bound DMT-on oligomeric compound was then incubated in concentrated aqueous ammonium hydroxide (80 mL/mmol) at 55° C. for 7 to 11 hours to cleave the oligomeric compound from the solid support and also deprotect nucleobases. The cleaved solution was allowed to cool to ambient temperature (20° C.) and the solution containing the oligomeric compound was filtered from the solid support. The solid support was then rinsed with water (160 mL/mmol) and filtered twice. The filtrates were combined and subjected to optical density (OD) measurement by UV and further analyzed by IP-HPLC-UV-MS to determine purity and yield.

The final detritylation and purification steps can further be conducted per procedures described by Capaldi, D. C. and Scozzari, A. N. Antisense Drug Discovery: Principles, Strategies and Applications (Crooke, S. T., Ed.) 2007, 2nd Ed., 401-434, CRC Press, Taylor and Francisco Group.

calculated bed height based on a 9.6 mL/g packing density. The column locking mechanisms were secured and connected to the synthesizer.

The appropriate reservoirs were charged with detritylation solution, phosphoramidite solutions, activator solution, sulfurization solution, capping solution A, capping solution B, phosphorus-deprotection solution, acetonitrile and toluene.

The support-bound Unylinker™ was swelled with toluene and immediately treated with the detritylation solution containing 10% DCA in toluene to provide free hydroxyl groups. After detritylation, the solid phase was washed with acetonitrile twice.

The solid phase was treated with a coupling solution having a total of 1.75 equivalents of phosphoramidite per coupling. The selected phosphoramidite solution is automatically mixed with the activator solution in a 1:1 volumetric ratio by the automated synthesizer before entering the synthesis column. The exiting coupling solution was then recycled through the solid phase via a recirculation loop to ensure sufficient time for the incorporation of the phosphoramidite monomer subunit. The solid phase was then washed with acetonitrile.

The solid phase was then treated with an aged PADS solution containing 0.2 M PADS in acetonitrile/3-picoline to con-

| Method A Step | Synthesis Step | Cycle | Volume (mL/mmol) | Flow (mL/min/mmol) | Target Delivery (min) | Equiv rel. to support loading |
|---|---|---|---|---|---|---|
| A | Detritylation | 1 | 89.1 | 23.1 | 3.9 | 108 |
|   |   | 2-16 | 63.7 | 23.1 | 2.8 | 77 |
|   |   | 17-20 | 69.5 | 23.1 | 3.0 | 84 |
| D | Coupling | 1-20 | 8.8 | 4.40 | 2.0 + 3.0 recirc | 1.75 |
|   | Coupling Activation | 1-20 | 8.8 | 4.40 | 2.0 + 3.0 recirc | 8.80 |
| F | Sulfurization | 1-20 | 32.4 | 10.1 | 3.2 | 6.5 |
| H | Capping | 1 | 81.0 | 10.8 | 7.5 + 7.5 recirc | 86 |
|   |   | 2-19 | 16.2 | 10.8 | 1.5 | 17 |
| J | Phosphorus Deprotection | NA | 46.3 | 23.1 | 2.0 + 30 – 120 recirc. | 9 |

In addition, the synthesis of 5-10-5 MOE gapmer-1 was also performed at a 550 mmol scale on a GE Healthcare OligoProcess synthesizer using a similar protocol as described above. After cleavage the solution containing the oligomeric compound was allowed to cool to ambient temperature (20° C.) and filtered from the solid support. The solid support was then rinsed with twice with water (160 mL/mmol) and filtered. The combined filtrates were concentrated under vacuo until a pH of 10.3 was obtained and analyzed in the same manner as described above.

EXAMPLE 7

Preparation of 5-10-5 MOE Gapmer-1 with Each Capping Step "H" Eliminated (Method B)

Synthesis of 5-10-5 MOE gapmer-1 from Example 6 was performed on an ÄKTA OligoPilot 100 synthesizer at a 2.0 mmol scale using the procedures set forth below. The synthesis was performed with the capping step "H" eliminated for each step throughout the oligonucleotide synthesis. (Method B).

6.08 g of a Primer Support 5G support-bound Unylinker™ (2.0 mmol loading) was weighed into the synthesis column and slurried in acetonitrile. The piston was lowered to the vert phosphite triester internucleoside linkages into thiophosphate triester internucleoside linkages. After sulfurization, the solid phase was washed with acetonitrile.

Each of the capping steps were omitted and replaced with toluene wash steps for the 19 iterative coupling cycles.

The solid support-bound DMT-on oligomeric compound was treated with a phosphorus deprotection solution containing a 1:1 volumetric ratio of TEA and acetonitrile. The exiting phosphorus deprotection solution was then recycled through the solid phase via a recirculation loop to ensure sufficient time to remove the CNET protecting groups. After deprotection the solid phase was washed with toluene.

The solid support was removed from the column and dried per established procedures. The support bound DMT-on oligomeric compound was then incubated in concentrated aqueous ammonium hydroxide (80 mL/mmol) at 55° C. for 7 to 11 hours to cleave the oligomeric compound from the solid support and also deprotect nucleobases. The cleaved solution was allowed to cool to ambient temperature (20° C.) and the solution containing the oligomeric compound was filtered from the solid support. The solid support was then rinsed with water (160 mL/mmol) and filtered twice. The filtrates were combined and subjected to optical density (OD) measurement by UV and further analyzed by IP-HPLC-UV-MS to determine purity and yield.

| Method B Step | Synthesis Step | Cycle | Volume (mL/mmol) | Flow (mL/min/mmol) | Target Delivery (min) | Equiv. rel. to support loading |
|---|---|---|---|---|---|---|
| B | Detritylation | 1 | 89.1 | 23.1 | 3.9 | 108 |
| | | 2-16 | 63.7 | 23.1 | 2.8 | 77 |
| | | 17-20 | 69.5 | 23.1 | 3.0 | 84 |
| D | Coupling | 1-20 | 8.8 | 4.40 | 2.0 + 3.0 recirc | 1.75 |
| | Coupling Activation | 1-20 | 8.8 | 4.40 | 2.0 + 3.0 recirc | 8.80 |
| F | Sulfurization | 1-20 | 32.4 | 10.1 | 3.2 | 6.5 |
| H | Capping | 1 | 0 | 0 | 0 | 0 |
| | | 2-19 | 2 | 0 | 0 | 0 |
| J | Phosphorus Deprotection | NA | 46.3 | 23.1 | 2.0 + 30 – 120 recirc | 9. |

EXAMPLE 8

Preparation of 5-10-5 MOE Gapmer-1 Using Half of the Standard Equivalents of Acetic Anhydride for Each Capping Step "H" (Method C)

Synthesis of 5-10-5 MOE gapmer-1 from Example 6 was performed on an ÄKTA OligoPilot 100 synthesizer at a 2.0 mmol scale using the procedures set forth below. The synthesis was performed using the modified method by reducing standard capping equivalents of acetic anhydride to half for capping step "H" (Method C).

6.08 g of a Primer Support 5G support-bound Unylinker™ (2.0 mmol; 329 µmol/g loading value) was weighed into the synthesis column and slurried in acetonitrile. The piston was lowered to the calculated bed height based on a 9.6 mL/g packing density. The column locking mechanisms were secured and connected to the synthesizer.

The appropriate reservoirs were charged with detritylation solution, phosphoramidite solutions, activator solution, sulfurization solution, capping solution A, capping solution B, phosphorus-deprotection solution, acetonitrile and toluene.

The support-bound Unylinker™ was swelled with toluene and immediately treated with the detritylation solution containing 10% DCA in toluene to provide free hydroxyl groups. After detritylation, the solid phase was washed with acetonitrile twice.

The solid phase was treated with a coupling solution having a total of 1.75 equivalents of phosphoramidite per coupling. The selected phosphoramidite solution is automatically mixed with the activator solution in a 1:1 volumetric ratio by the automated synthesizer before entering the synthesis column. The exiting coupling solution was then recycled through the solid phase via a recirculation loop to ensure sufficient time for the incorporation of the phosphoramidite monomer subunit. The solid phase was then washed with acetonitrile.

The solid phase was treated with an aged PADS solution containing 0.2 M PADS in acetonitrile/3-picoline to convert phosphite triester internucleoside linkages into thiophosphate triester internucleoside linkages. After sulfurization, the solid phase was washed with acetonitrile.

The solid phase was then treated with a mixture of capping reagents having half of the standard number of equivalents of acetic anhydride. The capping solution provided 43 equivalents of acetic anhydride for the first cycle (capping of unreacted hydroxyl groups on the Unylinker™ groups) and 8.5 equivalents per phosphoramidite coupling thereafter, except for the final cycle. Capping reagent A is automatically mixed with the capping reagent B in a 1:1 volumetric ratio by the automated synthesizer before entering the synthesis column. The exiting capping solution was recycled through the solid phase via a recirculation loop for the first cycle.

After capping, the solid phase was washed with toluene. The iterative cycle was repeated 19 times to prepare the 5-10-5 MOE gapmer on the solid support.

After the desired sequence was assembled, the support-bound DMT-on oligomeric compound was treated with a phosphorus deprotection solution containing a 1:1 volumetric ration of TEA and acetonitrile. The exiting phosphorus deprotection solution was then recycled through the solid phase via a recirculation loop to ensure sufficient time to remove the CNET protecting groups. After phosphorus deprotection the solid phase was washed with toluene.

The solid support was removed from the column and dried per established procedures. The support bound DMT-on oligomeric compound was then incubated in concentrated aqueous ammonium hydroxide (80 mL/mmol) at 55° C. for 7 to 11 hours to cleave the oligomeric compound from the solid support and also deprotect nucleobases. The cleaved solution was allowed to cool to ambient temperature (20° C.) and the solution containing the oligomeric compound was filtered from the solid support. The solid support was then rinsed with water (160 mL/mmol) and filtered twice. The filtrates were combined and subjected to optical density (OD) measurement by UV and further analyzed by IP-HPLC-UV-MS to determine purity and yield.

| Method C Step | Synthesis Step | Cycle | Volume (mL/mmol) | Flow (mL/min/mmol) | Target Delivery (min) | Equiv. rel. to support loading |
|---|---|---|---|---|---|---|
| B | Detritylation | 1 | 89.1 | 23.1 | 3.9 | 108 |
| | | 2-16 | 63.7 | 23.1 | 2.8 | 77 |
| | | 17-20 | 69.5 | 23.1 | 3.0 | 84 |
| D | Coupling | 1-20 | 8.8 | 4.40 | 2.0 + 3.0 recirc | 1.75 |
| | Coupling Activation | 1-20 | 8.8 | 4.40 | 2.0 + 3.0 recirc | 8.80 |

-continued

| Method C Step | Synthesis Step | Cycle | Volume (mL/mmol) | Flow (mL/min/mmol) | Target Delivery (min) | Equiv. rel. to support loading |
|---|---|---|---|---|---|---|
| F | Sulfurization | 1-20 | 32.4 | 10.1 | 3.2 | 6.5 |
| H | Capping | 1 | 81.0 | 10.8 | 7.5 + 7.5 recirc | 43 |
|   |   | 2-19 | 16.2 | 10.8 | 1.5 | 8.5 |
| J | Phosphorus Deprotection | NA | 46.3 | 23.1 | 2.0 + 30 – 120 recirc | 9. |

In addition, the synthesis of 5-10-5 MOE gapmer-1 was also performed at a 550 mmol scale on a GE Healthcare OligoProcess synthesizer using a similar protocol as described above. After cleavage the solution containing the oligomeric compound was allowed to cool to ambient temperature (20° C.) and filtered from the solid support. The solid support was then rinsed with twice with water (160 mL/mmol) and filtered. The combined filtrates were concentrated under vacuo until a pH of 10.3 was obtained and analyzed in the same manner as described above.

EXAMPLE 9

General Procedure for Analyzing a Crude Sample after Cleavage from Solid Support Analysis of a crude, DMT-on product is conducted by Ion-pair reverse phased High Performance Liquid Chromatography with Ultraviolet detection coupled to Mass Spectrometry (IP-HPLC-UV-MS) using Agilent 1100 Series and Water's XBridge C18 3.5 µM column (2.1 mm×150 mm) with part number 186003023. Mobile Phase A comprises J.T. Baker Water with 10% acetonitrile, 5 mM TBuAA (tributylammonium acetate), and 1 µM EDTA (ethylenediaminetetraacetic acid). Mobile Phase B comprises J.T. Baker Water with 80% acetonitrile, 5 mM TBuAA and 1 µM EDTA.

IP-HPLC-UV-MS methods are used to analyze the crude, DMT-on product after cleavage from a support medium. The general gradient conditions are shown below.

| Time (min) | Mobile Phase A (%) | Mobile Phase B (%) | Flow Rate (mL/min/mmol) |
|---|---|---|---|
| 0.00 | 55.00 | 45.00 | 0.250 |
| 22.00 | 20.00 | 80.00 | 0.250 |
| 30.00 | 20.00 | 80.00 | 0.250 |
| 31.00 | 55.00 | 45.00 | 0.250. |

IP-HPLC-UV-MS Analysis

Add a sample of crude solution to a tared centrifuge tube, record sample mass, vacuum centrifuge at ambient temperature to dryness, and reconstitute in a known mass of 0.01% TEA in water. Generally, 25 mg of crude is reconstituted in 2000 mg of 0.01% TEA. An appropriate concentration of 2.5 $AU_{260}$/mL is generally an appropriate goal for the dilution. Analyze the crude sample by IP-HPLC-UV-MS to determine purity and yield.

The impurity profile of oligonucleotides is determined by IP-HPLC-UV-MS. It is not possible to resolve all of the impurities from the parent oligonucleotide by IP-HPLC-UV; therefore all components that elute within the main UV peak are quantified by mass spectrometry. This is accomplished by extracting the ion currents due to all components that elute within the main UV peak. Taking average mass spectrum under the main UV peak gives an overview of the mass spectral dimension of the impurity profile at a glance. Overlay of average mass spectra from control and experimental samples provides an overall picture of the shift in impurities eluting under the main UV peak.

EXAMPLE 10

Crude Sample Analysis and Comparison of Method a (Standard Capping) to Method B (No Capping) for 5-10-5 MOE Gapmer-1

The synthesis of 5-10-5 MOE gapmer-1 on a 2.0 mmol scale utilizing Methods A and B was exemplified in Examples 6 and 7. The crude samples were prepared for analysis utilizing the procedure as illustrated in Example 9. Only components that elute within the main UV peak are quantified and reported. Results of the syntheses from Methods A and B are compared and presented below (also see FIGS. 1-3).

As illustrated, the capping reaction itself appears to detritylate and cap the growing oligonucleotides to a small extent, causing a gradual reduction in yield as the capping equivalent increases in standard coupling condition (Method A). Thus, eliminating the capping step entirely throughout the oligonucleotide synthesis (Method B) reduced the main UV peak capping related impurities $(P=O)_1$, Depyrimidination, Unknown (n+41/42), Unknown (n+68/72), Unknown (n+82/84), and Unknown (n+98 amu) as compared to control Method A. Further, improvement in yield and purity of full length crude oligonucleotide was also achieved.

Although a minimal increase in the total main UV peak impurities was observed which is believed to derive from the increase in total n−1 impurity that are mainly composed of n−$1^{st}$ coupled base to the Primer Support 5G UnyLinker solid-support, the n−1 impurity level can be partially mitigated by reducing the capping equivalents and utilizing solid support other than Primer Support 5G as exemplified in Examples 12 and 14, respectively.

| Capping Conditions | Std Capping (control) | No Capping |
|---|---|---|
| Method | A | B |
| Scale (mmol) | 2.0 | 2.0 |
| Solid support | Primer Support 5G | Primer Support 5G |
| UnyLinker Capping Equivalent | 86 | 0 |
| Non-UnyLinker Capping Equivalent | 17 | 0 |

| Yield and Purity (%) | Std Capping (control) | No Capping |
|---|---|---|
| Yield | 63.4 | 69.4 |
| UV Purity | 77.5 | 81.5 |

| Capping Related Impurities (%) | Std Capping (control) | No Capping |
|---|---|---|
| Depyrimidination | 0.3 | None Detected (<0.10) |
| (P=O)$_1$ | 1.2 | 0.7 |
| Unknown (n + 41/42) | 0.2 | None Detected (<0.10) |
| Unknown (n + 68/72) | 0.4 | 0.2 |
| Unknown (n + 82/84) | 0.4 | 0.1 |
| Unknown (n + 98) | 0.3 | 0.2 |
| Total Main UV Peak Capping Related Impurities | 2.8 | 1.2 |

| Main UV Peak Impurities (%) | Std Capping (control) | No Capping |
|---|---|---|
| Total n−1 | 1.1 | 3.4 |
| Depurination | 0.2 | 0.2 |
| Total Other Impurities | 3.9 | 4.1 |
| Total Capping Related Impurities | 2.8 | 1.2 |
| Total n + 1 | 0.5 | 0.4 |
| Total Main UV Peak Impurities | 8.5 | 9.3 |

EXAMPLE 11

Crude Sample Analysis and Comparison of Method a (Standard Capping) to Method C (½ Capping) for 5-10-5 MOE Gapmer-1

The synthesis of 5-10-5 MOE gapmer-1 was performed in the same manner as exemplified in Examples 6 and 8 on a 550 mmol scale using both Methods A and C. The crude samples were prepared for analysis using the procedure as illustrated in Example 9. Only components that elute within the main UV peak are quantified and reported. Results of the syntheses from Methods A and C are compared and presented below (also see FIGS. 4-6).

As illustrated, the capping reaction itself appears to have detritylated and capped the growing oligonucleotides to a small extent, causing a gradual reduction in yield as the capping equivalent increased in standard coupling condition (Method A). Thus, reducing the capping equivalent to half (Method C) resulted in a decrease in the total main UV peak impurities of the crude oligonucleotide on a 550 mmol scale on Primer Support 5G UnyLinker solid support. A reduction in main UV peak capping related impurities (P=O)$_1$, Depyrimidination, Unknown (n+41/42), Unknown (n+68/72), Unknown (n+82/84), and Unknown (n+98 amu) was obtained. Further, improvement in yield and purity of full length crude oligonucleotide was also achieved with modified Method C.

| Capping Conditions | Std Capping (control) | ½ Capping (reduced) |
|---|---|---|
| Method | A | C |
| Scale (mmol) | 550 | 550 |
| Solid support | Primer Support 5G | Primer Support 5G |
| UnyLinker Capping Equivalent | 86 | 43 |
| Non-UnyLinker Capping Equivalent | 17 | 8.5 |

| Yield and Purity (%) | Std Capping (control) | ½ Capping (reduced) |
|---|---|---|
| Yield | 63.5 | 66.7 |
| UV Purity | 80.3 | 82.5 |

| Capping Related Impurities (%) | Std Capping (control) | ½ Capping (reduced) |
|---|---|---|
| Depyrimidination | 0.2 | 0.1 |
| (P=O)$_1$ | 1.1 | 0.9 |
| Unknown (n + 41/42) | 0.5 | 0.4 |
| Unknown (n + 68/72) | 0.4 | 0.3 |
| Unknown (n + 82/84) | 0.5 | 0.4 |
| Unknown (n + 98) | 0.4 | 0.2 |
| Total Main UV Peak Capping Related Impurities | 3.1 | 2.3 |

| Main UV Peak Impurities (%) | Std Capping (control) | ½ Capping (reduced) |
|---|---|---|
| Total n − 1 | 1.4 | 1.7 |
| Depurination | 0.4 | 0.3 |
| Total Other Impurities | 0.9 | 0.7 |
| Total Capping Related Impurities | 3.1 | 2.3 |
| Total n + 1 | 2.5 | 2.2 |
| Total Main UV Peak Impurities | 8.3 | 7.2 |

EXAMPLE 12

Crude Sample Analysis and Comparison of Method a (Standard Capping) to Method B (No Capping) for 5-10-5 MOE Gapmer-2

The synthesis of another sequence, 5-10-5 MOE gapmer-2 was carried out in the same manner as exemplified in Examples 6 and 7 on a 2.0 mmol scale using both Methods A and B. NittoPhase-HL Unylinker solid-support was used in place of Primer Support 5G. The crude samples were prepared for analysis using the procedure as illustrated in Example 9. Only components that elute within the main UV peak are quantified and reported. Results of the syntheses from Methods A and B are compared and presented below (also see FIGS. 7-9).

As illustrated, eliminating the capping step entirely throughout the oligonucleotide synthesis (Method B) using NittoPhase-HL UnyLinker solid support results in an improvement in yield, purity and the overall impurity profile of the full length crude oligonucleotide as compared to standard capping condition (Method A). Further, the increase in total n−1 impurity was not observed with NittoPhase-HL as observed with Primer Support 5G which may suggest that the first coupling of the phosphoramidite to NittoPhase-HL UnyLinker solid support was more efficient than with Primer Support 5G UnyLinker.

| Capping Conditions | Std Capping (control) | No Capping |
|---|---|---|
| Method | A | B |
| Scale (mmol) | 2.0 | 2.0 |
| Solid support | NittoPhase-HL | NittoPhase-HL |
| UnyLinker Capping Equivalent | 86 | 0 |
| Non-UnyLinker Capping Equivalent | 17 | 0 |

| Yield and Purity (%) | Std Capping (control) | No Capping |
|---|---|---|
| Yield | 64.7 | 69.3 |
| UV Purity | 81.1 | 85.2 |

| Capping Related Impurities (%) | Std Capping (control) | No Capping |
|---|---|---|
| Depyrimidation | 0.3 | None Detected (<0.10) |
| (P=O)$_1$ | 1.5 | 1.0 |
| Unknown (n + 41/42) | 0.4 | 0.2 |
| Unknown (n + 68/72) | 0.4 | 0.1 |
| Unknown (n + 82/84) | 0.6 | 0.1 |
| Unknown (n + 98) | 0.4 | 0.2 |
| Total Main UV Peak Capping Related Impurities | 3.6 | 1.6 |

| Main UV Peak Impurities (%) | Std Capping (control) | No Capping |
|---|---|---|
| Total n − 1 | 0.9 | 0.9 |
| Depurination | 0.2 | 0.1 |
| Total Other Impurities | 4.5 | 3.5 |
| Total Capping Related Impurities | 3.6 | 1.6 |
| Total n + 1 | 0.8 | 0.7 |
| Total Main UV Peak Impurities | 10.0 | 6.8. |

EXAMPLE 13

Crude Sample Analysis and Comparison of Method a (Standard Capping) to Method D (No Capping Except for UnyLinker) for 5-10-5 MOE Gapmer-3

The synthesis of an additional sequence, 5-10-5 MOE gapmer-3 was carried out in a similar manner as illustrated in Examples 6 and 8 on a 2.0 mmol scale using both Methods A and D. The crude samples were prepared for analysis as per the procedure illustrated in Example 9. Only components that elute within the main UV peak are quantified and reported. Results of the syntheses from Methods A and D are compared and presented below (also see FIGS. 10-12).

As illustrated, the capping reaction itself appeared to detritylate and cap the growing oligonucleotides to a small extent, causing a gradual reduction in yield as the capping equivalent increases. Thus, only capping the first synthesis cycle after UnyLinker coupling (Method D) at a 2 mmol synthesis on Primer Support 5G UnyLinker solid support resulted in a reduction in the main UV peak capping related impurities (P=O)$_1$, Depyrimidation, Unknown (n+68/72), Unknown (n+82/84), and Unknown (n+98 amu) as compared to standard capping (Method A). Further, an increase in yield and purity of the full length crude oligonucleotide was also obtained.

Although an increase in the total main UV peak impurities was observed which is believed to derive from the increase in total n−1 impurities that are mainly composed of n−1$^{st}$ coupled base to the Primer Support 5G UnyLinker solid-support, the n−1 impurity level can be partially mitigated by reducing the capping equivalents and utilizing solid support other than Primer Support 5G as exemplified in Examples 12 and 14, respectively.

| Capping Conditions | Std Capping (control) | No Capping (except for UnyLinker) |
|---|---|---|
| Method | A | B |
| Scale (mmol) | 2 | 2 |
| Solid support | Primer Support 5G | Primer Support 5G |
| UnyLinker Capping Equivalent | 86 | 86 |
| Non-UnyLinker Capping Equivalent | 17 | 0 |

| Yield and Purity (%) | Std Capping (control) | No Capping (except for UnyLinker) |
|---|---|---|
| Yield | 58.2 | 63.5 |
| UV Purity | 82.2 | 85.5 |

| Capping Related Impurities (%) | Std Capping (control) | No Capping (except for UnyLinker) |
|---|---|---|
| Depyrimidination | 0.2 | None Detected (<0.10) |
| (P=O)$_1$ | 1.4 | 1.3 |
| Unknown (n + 41/42) | None Detected (<0.10) | None Detected (<0.10) |
| Unknown (n + 68/72) | 0.4 | 0.2 |
| Unknown (n + 82/84) | 0.4 | 0.1 |
| Unknown (n + 98) | 0.8 | 0.4 |
| Total Main UV Peak Capping Related Impurities | 3.2 | 2.0 |

| Main UV Peak Impurities (%) | Std Capping (control) | No Capping (except for UnyLinker) |
|---|---|---|
| Total n − 1 | 1 | 3.5 |
| Depurination | 0.3 | 0.4 |
| Total Other Impurities | 2.3 | 3.3 |
| Total n + 1 | 1.2 | 0.7 |
| Total Capping Related Impurities | 3.2 | 2.0 |
| Total Main UV Peak Impurities | 8.0 | 9.9. |

EXAMPLE 14

Crude Sample Analysis and Comparison of Method a (Standard Capping) to Method B (No Capping), Method C (½ Capping) and Method E (¼ Capping) for 5-10-5 MOE Gapmer-4

The synthesis of an additional sequence, 5-10-5 MOE gapmer-4 was carried out in the same manner as illustrated in Examples 6, 7 and 8 on a 2.2 mmol scale using Methods A, B, C and E. NittoPhase-HL Unylinker solid-support was used in place of Primer Support 5G. The crude samples were prepared for analysis as per the procedure illustrated in Example 9. Only components that elute within the main UV peak are quantified and reported. Results of the syntheses from Methods A, B, C and E are compared and presented below (also see FIGS. 13-17).

As illustrated, eliminating the capping step throughout the oligonucleotide synthesis (Method B) or reducing the equivalents of capping solution (Methods C and E) when using NittoPhase-HL UnyLinker solid support resulted in an improvement in yield, purity and the overall impurity profile of the full length crude oligonucleotide as compared to standard capping condition (Method A). Further, the increase in total n−1 impurity was not observed with NittoPhase-HL as observed with Primer Support 5G. This result may suggest that the first coupling of the phosphoramidite to NittoPhase-HL UnyLinker solid support was more efficient than with Primer Support 5G UnyLinker.

| Capping Conditions | All Capping (control) | ½ Capping (reduced) | ¼ Capping (reduced) | No Capping |
|---|---|---|---|---|
| Method | A | C | C | B |
| Scale (mmol) | 2.2 | 2.2 | 2.2 | 2.2 |

-continued

| Capping Conditions | All Capping (control) | ½ Capping (reduced) | ¼ Capping (reduced) | No Capping |
|---|---|---|---|---|
| Solid support | NittoPhase-HL | NittoPhase-HL | NittoPhase-HL | NittoPhase-HL |
| UnyLinker Capping Equivalent | 86 | 43 | 21.5 | 0 |
| Non-UnyLinker Capping Equivalent | 17 | 8.5 | 4.25 | 0 |

| Yield and Purity (%) | All Capping (control) | ½ Capping (reduced) | ¼ Capping (reduced) | No Capping |
|---|---|---|---|---|
| Yield | 61.8 | 67.6 | 69.1 | 70.6 |
| UV Purity | 77.3 | 83.4 | 84.8 | 85.6 |

| Capping Related Impurities (%) | All Capping (control) | ½ Capping (reduced) | ¼ Capping (reduced) | No Capping |
|---|---|---|---|---|
| Depyrimidination | 0.1 | None Detected | None Detected | None Detected |
| (P=O)$_1$ | 0.9 | 0.7 | 0.7 | 0.7 |
| Unknown (n + 41/42) | 0.4 | 0.3 | 0.3 | 0.3 |
| Unknown (n + 68/72) | 0.4 | 0.2 | 0.1 | 0.1 |
| Unknown (n + 82/84) | 0.6 | 0.3 | 0.2 | 0.1 |
| Unknown (n + 98) | 0.4 | 0.2 | 0.1 | 0.1 |
| Total Main UV Peak Capping Related Impurities | 2.8 | 1.7 | 1.4 | 1.3 |

| Main UV Peak Impurities (%) | All Capping (control) | ½ Capping (reduced) | ¼ Capping (reduced) | No Capping |
|---|---|---|---|---|
| Total n − 1 | 0.8 | 0.9 | 0.9 | 0.9 |
| Depurination | 0.3 | 0.2 | 0.1 | 0.1 |
| Total Other Impurities | 2.5 | 1.8 | 1.8 | 1.7 |
| Capping Related Impurities | 2.8 | 1.7 | 1.4 | 1.3 |
| Total n + 1 | 1.3 | 1.2 | 1.1 | 1.0 |
| Total Main UV Peak Impurities | 7.7 | 5.8 | 5.3 | 5.0. |

EXAMPLE 15

Comparison of Method a (Standard Capping) to Method B (No Capping), Method C (½ Capping), Method D (No Capping Except for Unylinker) or Method E (¼ Capping) for the Synthesis of Oligomeric Compounds As illustrated in Examples 10-14, the capping reaction itself appears to detritylate and cap the growing oligonucleotides to a small extent, causing a gradual reduction in yield as the capping equivalent increases in standard coupling condition (Method A). Thus, eliminating or reducing capping using the modified methods B-E demonstrated an improvement in yield, purity and the capping related impurity profile of the full length crude oligonucleotide (Tables 1-8).

Although an increase in total n−1 impurity was observed in some instances when Primer Support 5G Unylinker solid support was utilized, the n−1 impurity level can be partially mitigated by reducing the capping equivalents and utilizing solid support other than Primer Support 5G (PS 5G).

TABLE 1

Impact of capping on crude synthesis yield and UV purity

| Oligo | Scale (mmol) | Solid Support | Capping Condition | Cycle | Equiv | Yield (%) | UV Purity (%) |
|---|---|---|---|---|---|---|---|
| Gapmer-1 | 2.0 | PS 5G | Std Capping | 1 | 86 | 63.4 | 77.5 |
| | | | | 2-19 | 17 | | |
| Gapmer-1 | 2.0 | PS 5G | No Capping | 1 | 0 | 69.4 | 81.5 |
| | | | | 2-19 | 0 | | |
| Gapmer-1 | 550 | PS 5G | Std Capping | 1 | 86 | 63.5 | 80.3 |
| | | | | 2-19 | 17 | | |
| Gapmer-1 | 550 | PS 5G | ½ Capping | 1 | 43 | 66.7 | 82.5 |
| | | | | 2-19 | 8.5 | | |
| Gapmer-2 | 2.0 | NittoPhase-HL | Std Capping | 1 | 86 | 64.7 | 81.1 |
| | | | | 2-19 | 17 | | |
| Gapmer-2 | 2.0 | NittoPhase-HL | No Capping | 1 | 0 | 69.3 | 85.2 |
| | | | | 2-19 | 0 | | |
| Gapmer-3 | 2.0 | PS 5G | Std Capping | 1 | 86 | 58.2 | 82.2 |
| | | | | 2-19 | 17 | | |

TABLE 1-continued

Impact of capping on crude synthesis yield and UV purity

| Oligo | Scale (mmol) | Solid Support | Capping Condition | Cycle | Equiv | Yield (%) | UV Purity (%) |
|---|---|---|---|---|---|---|---|
| Gapmer-3 | 2.0 | PS 5G | Only UnyLinker Capping | 1<br>2-19 | 86<br>0 | 63.5 | 85.5 |
| Gapmer-4 | 2.2 | NittoPhase-HL | Std Capping | 1<br>2-19 | 86<br>17 | 61.8 | 77.3 |
| Gapmer-4 | 2.2 | NittoPhase-HL | ½ Capping | 1<br>2-19 | 43<br>8.5 | 67.6 | 83.4 |
| Gapmer-4 | 2.2 | NittoPhase-HL | ¼ Capping | 1<br>2-19 | 21.5<br>4.25 | 69.1 | 84.8 |
| Gapmer-4 | 2.2 | NittoPhase-HL | No Capping | 1<br>2-19 | 0<br>0 | 70.6 | 85.6. |

TABLE 2

Impact of capping on Total (n-1)

| Oligo | Scale (mmol) | Support | Capping Condition | Cycle | Equiv | Total n-1 (%) |
|---|---|---|---|---|---|---|
| Gapmer-1 | 2.0 | PS 5G | Std Capping | 1<br>2-19 | 86<br>17 | 1.1 |
| Gapmer-1 | 2.0 | PS 5G | No Capping | 1<br>2-19 | 0<br>0 | 3.4 |
| Gapmer-1 | 550 | PS 5G | Std Capping | 1<br>2-19 | 86<br>17 | 1.4 |
| Gapmer-1 | 550 | PS 5G | ½ Capping | 1<br>2-19 | 43<br>8.5 | 1.7 |
| Gapmer-2 | 2.0 | NittoPhase-HL | Std Capping | 1<br>2-19 | 86<br>17 | 0.9 |
| Gapmer-2 | 2.0 | NittoPhase-HL | No Capping | 1<br>2-19 | 0<br>0 | 0.9 |
| Gapmer-3 | 2.0 | PS 5G | Std Capping | 1 | 86 | 1.0 |
| Gapmer-3 | 2.0 | PS 5G | Only UnyLinker Capping | 1<br>2-19 | 86<br>0 | 3.5 |
| Gapmer-4 | 2.2 | NittoPhase-HL | Std Capping | 1<br>2-19 | 86<br>17 | 0.8 |
| Gapmer-4 | 2.2 | NittoPhase-HL | ½ Capping | 1<br>2-19 | 43<br>8.5 | 0.9 |
| Gapmer-4 | 2.2 | NittoPhase-HL | ¼ Capping | 1<br>2-19 | 21.5<br>4.25 | 0.9 |
| Gapmer-4 | 2.2 | NittoPhase-HL | No Capping | 1<br>2-19 | 0<br>0 | 0.9. |

TABLE 3

Impact of capping on Depyrimidation (Loss of $^{Me}C + H_2O$)

| Oligo | Scale (mmol) | Support | Capping Condition | Cycle | Equiv | Depyrimidation (%) |
|---|---|---|---|---|---|---|
| Gapmer-1 | 2.0 | PS 5G | Std Capping | 1<br>2-19 | 86<br>17 | 0.3 |
| Gapmer-1 | 2.0 | PS 5G | No Capping | 1<br>2-19 | 0<br>0 | None Detected (<0.10) |
| Gapmer-1 | 550 | PS 5G | Std Capping | 1<br>2-19 | 86<br>17 | 0.2 |
| Gapmer-1 | 550 | PS 5G | ½ Capping | 1<br>2-19 | 43<br>8.5 | 0.1 |
| Gapmer-2 | 2.0 | NittoPhase-HL | Std Capping | 1<br>2-19 | 86<br>17 | 0.3 |
| Gapmer-2 | 2.0 | NittoPhase-HL | No Capping | 1<br>2-19 | 0<br>0 | None Detected (<0.10) |
| Gapmer-3 | 2.0 | PS 5G | Std Capping | 1<br>2-19 | 86<br>17 | 0.2 |
| Gapmer-3 | 2.0 | PS 5G | Only UnyLinker Capping | 1<br>2-19 | 86<br>0 | None Detected (<0.10) |
| Gapmer-4 | 2.2 | NittoPhase-HL | Std Capping | 1<br>2-19 | 86<br>17 | 0.1 |
| Gapmer-4 | 2.2 | NittoPhase-HL | ½ Capping | 1<br>2-19 | 43<br>8.5 | None Detected (<0.10) |
| Gapmer-4 | 2.2 | NittoPhase-HL | ¼ Capping | 1<br>2-19 | 21.5<br>4.25 | None Detected (<0.10) |
| Gapmer-4 | 2.2 | NittoPhase-HL | No Capping | 1<br>2-19 | 0<br>0 | None Detected. |

TABLE 4

Impact of capping on (P=O)₁

| Oligo | Scale (mmol) | Support | Capping Condition | Cycle | Equiv | (P=O)₁ (%) |
|---|---|---|---|---|---|---|
| Gapmer-1 | 2.0 | PS 5G | Std Capping | 1 | 86 | 1.2 |
|  |  |  |  | 2-19 | 17 |  |
| Gapmer-1 | 2.0 | PS 5G | No Capping | 1 | 0 | 0.7 |
|  |  |  |  | 2-19 | 0 |  |
| Gapmer-1 | 550 | PS 5G | Std Capping | 1 | 86 | 1.1 |
|  |  |  |  | 2-19 | 17 |  |
| Gapmer-1 | 550 | PS 5G | ½ Capping | 1 | 43 | 0.9 |
|  |  |  |  | 2-19 | 8.5 |  |
| Gapmer-2 | 2.0 | NittoPhase-HL | Std Capping | 1 | 86 | 1.5 |
|  |  |  |  | 2-19 | 17 |  |
| Gapmer-2 | 2.0 | NittoPhase-HL | No Capping | 1 | 0 | 1.0 |
|  |  |  |  | 2-19 | 0 |  |
| Gapmer-3 | 2.0 | PS 5G | Std Capping | 1 | 86 | 1.4 |
|  |  |  |  | 2-19 | 17 |  |
| Gapmer-3 | 2.0 | PS 5G | Only UnyLinker Capping | 1 | 86 | 1.3 |
|  |  |  |  | 2-19 | 0 |  |
| Gapmer-4 | 2.2 | NittoPhase-HL | Std Capping | 1 | 86 | 0.9 |
|  |  |  |  | 2-19 | 17 |  |
| Gapmer-4 | 2.2 | NittoPhase-HL | ½ Capping | 1 | 43 | 0.7 |
|  |  |  |  | 2-19 | 8.5 |  |
| Gapmer-4 | 2.2 | NittoPhase-HL | ¼ Capping | 1 | 21.5 | 0.7 |
|  |  |  |  | 2-19 | 4.25 |  |
| Gapmer-4 | 2.2 | NittoPhase-HL | No Capping | 1 | 0 | 0.7. |
|  |  |  |  | 2-19 | 0 |  |

TABLE 5

Impact of capping on Unknown (n + 41/42)

| Oligo | Scale (mmol) | Support | Capping Condition | Cycle | Equiv | (n + 41/42) (%) |
|---|---|---|---|---|---|---|
| Gapmer-1 | 2.0 | PS 5G | Std Capping | 1 | 86 | 0.2 |
|  |  |  |  | 2-19 | 17 |  |
| Gapmer-1 | 2.0 | PS 5G | No Capping | 1 | 0 | None Detected (<0.10) |
|  |  |  |  | 2-19 | 0 |  |
| Gapmer-1 | 550 | PS 5G | Std Capping | 1 | 86 | 0.5 |
|  |  |  |  | 2-19 | 17 |  |
| Gapmer-1 | 550 | PS 5G | ½ Capping | 1 | 43 | 0.4 |
|  |  |  |  | 2-19 | 8.5 |  |
| Gapmer-2 | 2.0 | NittoPhase-HL | Std Capping | 1 | 86 | 0.4 |
|  |  |  |  | 2-19 | 17 |  |
| Gapmer-2 | 2.0 | NittoPhase-HL | No Capping | 1 | 0 | 0.2 |
|  |  |  |  | 2-19 | 0 |  |
| Gapmer-3 | 2.0 | PS 5G | Std Capping | 1 | 86 | None Detected (<0.10) |
|  |  |  |  | 2-19 | 17 |  |
| Gapmer-3 | 2.0 | PS 5G | Only UnyLinker Capping | 1 | 86 | None Detected (<0.10) |
|  |  |  |  | 2-19 | 0 |  |
| Gapmer-4 | 2.2 | NittoPhase-HL | Std Capping | 1 | 86 | 0.4 |
|  |  |  |  | 2-19 | 17 |  |
| Gapmer-4 | 2.2 | NittoPhase-HL | ½ Capping | 1 | 43 | 0.3 |
|  |  |  |  | 2-19 | 8.5 |  |
| Gapmer-4 | 2.2 | NittoPhase-HL | ¼ Capping | 1 | 21.5 | 0.3 |
|  |  |  |  | 2-19 | 4.25 |  |
| Gapmer-4 | 2.2 | NittoPhase-HL | No Capping | 1 | 0 | 0.3. |
|  |  |  |  | 2-19 | 0 |  |

TABLE 6

Impact of capping on Unknown (n + 68/72)

| Oligo | Scale (mmol) | Support | Capping Condition | Cycle | Equiv | (n + 68/72) (%) |
|---|---|---|---|---|---|---|
| Gapmer-1 | 2.0 | PS 5G | Std Capping | 1 | 86 | 0.4 |
|  |  |  |  | 2-19 | 17 |  |
| Gapmer-1 | 2.0 | PS 5G | No Capping | 1 | 0 | 0.2 |
|  |  |  |  | 2-19 | 0 |  |
| Gapmer-1 | 550 | PS 5G | Std Capping | 1 | 86 | 0.4 |
|  |  |  |  | 2-19 | 17 |  |

TABLE 6-continued

Impact of capping on Unknown (n + 68/72)

| Oligo | Scale (mmol) | Support | Capping Condition | Cycle | Equiv | (n + 68/72) (%) |
|---|---|---|---|---|---|---|
| Gapmer-1 | 550 | PS 5G | ½ Capping | 1 | 43 | 0.3 |
| | | | | 2-19 | 8.5 | |
| Gapmer-2 | 2.0 | NittoPhase-HL | Std Capping | 1 | 86 | 0.4 |
| | | | | 2-19 | 17 | |
| Gapmer-2 | 2.0 | NittoPhase-HL | No Capping | 1 | 0 | 0.1 |
| | | | | 2-19 | 0 | |
| Gapmer-3 | 2.0 | PS 5G | Std Capping | 1 | 86 | 0.4 |
| | | | | 2-19 | 17 | |
| Gapmer-3 | 2.0 | PS 5G | Only UnyLinker Capping | 1 | 86 | 0.2 |
| | | | | 2-19 | 0 | |
| Gapmer-4 | 2.2 | NittoPhase-HL | Std Capping | 1 | 86 | 0.4 |
| | | | | 2-19 | 17 | |
| Gapmer-4 | 2.2 | NittoPhase-HL | ½ Capping | 1 | 43 | 0.2 |
| | | | | 2-19 | 8.5 | |
| Gapmer-4 | 2.2 | NittoPhase-HL | ¼ Capping | 1 | 21.5 | 0.1 |
| | | | | 2-19 | 4.25 | |
| Gapmer-4 | 2.2 | NittoPhase-HL | No Capping | 1 | 0 | 0.1. |
| | | | | 2-19 | 0 | |

TABLE 7

Impact of capping on Unknown (n + 82/84)

| Oligo | Scale (mmol) | Support | Capping Condition | Cycle | Equiv | (n + 82/84) (%) |
|---|---|---|---|---|---|---|
| Gapmer-1 | 2.0 | PS 5G | Std Capping | 1 | 86 | 0.4 |
| | | | | 2-19 | 17 | |
| Gapmer-1 | 2.0 | PS 5G | No Capping | 1 | 0 | 0.1 |
| | | | | 2-19 | 0 | |
| Gapmer-1 | 550 | PS 5G | Std Capping | 1 | 86 | 0.5 |
| | | | | 2-19 | 17 | |
| Gapmer-1 | 550 | PS 5G | ½ Capping | 1 | 43 | 0.4 |
| | | | | 2-19 | 8.5 | |
| Gapmer-2 | 2.0 | NittoPhase-HL | Std Capping | 1 | 86 | 0.6 |
| | | | | 2-19 | 17 | |
| Gapmer-2 | 2.0 | NittoPhase-HL | No Capping | 1 | 0 | 0.1 |
| | | | | 2-19 | 0 | |
| Gapmer-3 | 2.0 | PS 5G | Std Capping | 1 | 86 | 0.4 |
| | | | | 2-19 | 17 | |
| Gapmer-3 | 2.0 | PS 5G | Only UnyLinker Capping | 1 | 86 | 0.1 |
| | | | | 2-19 | 0 | |
| Gapmer-4 | 2.2 | NittoPhase-HL | Std Capping | 1 | 86 | 0.6 |
| | | | | 2-19 | 17 | |
| Gapmer-4 | 2.2 | NittoPhase-HL | ½ Capping | 1 | 43 | 0.3 |
| | | | | 2-19 | 8.5 | |
| Gapmer-4 | 2.2 | NittoPhase-HL | ¼ Capping | 1 | 21.5 | 0.2 |
| | | | | 2-19 | 4.25 | |
| Gapmer-4 | 2.2 | NittoPhase-HL | No Capping | 1 | 0 | 0.1. |
| | | | | 2-19 | 0 | |

TABLE 8

Impact of capping on Unknown (n + 98)

| Oligo | Scale (mmol) | Support | Capping Condition | Cycle | Equiv | (n + 98) (%) |
|---|---|---|---|---|---|---|
| Gapmer-1 | 2.0 | PS 5G | Std Capping | 1 | 86 | 0.3 |
| | | | | 2-19 | 17 | |
| Gapmer-1 | 2.0 | PS 5G | No Capping | 1 | 0 | 0.2 |
| | | | | 2-19 | 0 | |
| Gapmer-1 | 550 | PS 5G | Std Capping | 1 | 86 | 0.4 |
| | | | | 2-19 | 17 | |
| Gapmer-1 | 550 | PS 5G | ½ Capping | 1 | 43 | 0.2 |
| | | | | 2-19 | 8.5 | |
| Gapmer-2 | 2.0 | NittoPhase-HL | Std Capping | 1 | 86 | 0.4 |
| | | | | 2-19 | 17 | |
| Gapmer-2 | 2.0 | NittoPhase-HL | No Capping | 1 | 0 | 0.2 |
| | | | | 2-19 | 0 | |

TABLE 8-continued

Impact of capping on Unknown (n + 98)

| Oligo | Scale (mmol) | Support | Capping Condition | Cycle | Equiv | (n + 98) (%) |
|---|---|---|---|---|---|---|
| Gapmer-3 | 2.0 | PS 5G | Std Capping | 1 | 86 | 0.8 |
|  |  |  |  | 2-19 | 17 |  |
| Gapmer-3 | 2.0 | PS 5G | Only UnyLinker Capping | 1 | 86 | 0.4 |
|  |  |  |  | 2-19 | 0 |  |
| Gapmer-4 | 2.2 | NittoPhase-HL | Std Capping | 1 | 86 | 0.4 |
|  |  |  |  | 2-19 | 17 |  |
| Gapmer-4 | 2.2 | NittoPhase-HL | ½ Capping | 1 | 43 | 0.2 |
|  |  |  |  | 2-19 | 8.5 |  |
| Gapmer-4 | 2.2 | NittoPhase-HL | ¼ Capping | 1 | 21.5 | 0.1 |
|  |  |  |  | 2-19 | 4.25 |  |
| Gapmer-4 | 2.2 | NittoPhase-HL | No Capping | 1 | 0 | 0.1. |
|  |  |  |  | 2-19 | 0 |  |

What is claimed is:

1. A method of preparing an oligomeric compound comprising:
   a) providing a solid support having a plurality of monomer subunits linked thereto wherein each of the monomer subunits comprises a blocked hydroxyl group;
   b) deblocking the blocked hydroxyl groups to provide free hydroxyl groups;
   c) coupling further monomer subunits to the free hydroxyl groups, wherein each further monomer subunit comprises a phosphoramidite group and a blocked hydroxyl group, to the free hydroxyl groups to provide phosphite triester linked monomer subunits;
   d) oxidizing or sulfurizing the phosphite triester linked monomer subunits to provide phosphate triester or thiophosphate triester linked monomer subunits;
   e) optionally treating the phosphate triester or thiophosphate triester linked monomer subunits with a mixture of capping reagents to block any unreacted free hydroxyl groups;
   f) iteratively repeating steps b) through e) a predetermined number of times to provide the oligomeric compound; and
   wherein:
   the last iterative step e) is omitted and at least one iterative step e) is performed using a mixture of capping reagents having about 8.5 equivalents or less of acetic anhydride based on the loading of the solid support; or
   the last iterative step e) is omitted and each of the remaining iterative steps e) is performed using a mixture of capping reagents having about 8.5 equivalents or less of acetic anhydride based on the loading of the solid support; or
   each iterative step e) is performed and at least one iterative step e) is performed using a mixture of capping reagents having about 8.5 equivalents or less of acetic anhydride based on the loading of the solid support.

2. The method of claim 1 wherein the solid support is crosslinked polystyrene selected from Primer Support 5G or NittoPhaseHL.

3. The method of claim 1 wherein the solid support is a Unylinker# functionalized solid support.

4. The method of claim 1 wherein each monomer subunit is a nucleoside.

5. The method of claim 1 wherein each hydroxyl blocking group is 4,4'-dimethoxytrityl and each phosphoramidite group is a diisopropylcyanoethoxy phosphoramidite (—P(N[C(H)(CH$_3$)$_2$]$_2$)(O(CH$_2$)$_2$CN).

6. The method of claim 1 wherein dichloroacetic acid in toluene is used to deblock blocked hydroxyl groups.

7. The method of claim 1 wherein at least the last iterative step e) is omitted.

8. The method of claim 1 wherein iterative step e) is performed for about the first 50% of the iterative steps b) through e) and omitted for the remaining iterative steps b) through e).

9. The method of claim 1 wherein iterative step e) is performed for about the first 75% of the iterative steps b) through e) and omitted for the remaining iterative steps b) through e).

10. The method of claim 1 wherein each iterative step e) is performed.

11. The method of claim 1 wherein the mixture of capping reagents used for essentially each iterative capping step e) that is performed comprises about 8.5 equivalents or less of acetic anhydride based on the loading of the solid support.

12. The method of claim 1 wherein the mixture of capping reagents used for each iterative capping step e) that is performed comprises about 6 equivalents of acetic anhydride based on the loading of the solid support.

13. The method of claim 1 wherein the mixture of capping reagents used for each iterative capping step e) that is performed comprises about 4 equivalents of acetic anhydride based on the loading of the solid support.

14. The method of claim 1 wherein the mixture of capping reagents used for each iterative capping step e) that is performed comprises about 2 equivalents of acetic anhydride based on the loading of the solid support.

15. The method of claim 1 wherein the mixture of capping reagents used for each iterative capping step e) that is performed comprises less than 1 equivalent of acetic anhydride based on the loading of the solid support.

16. The method of claim 1 wherein the volume of the mixture of capping reagents is modified independently for each cycle of steps b) through e) such that about 17 equivalents of acetic anhydride are used for the first cycle and over each successive cycle that includes the capping step e) the equivalents of acetic anhydride are serially reduced to about 1 equivalent based on the loading of the solid support.

17. The method of claim 1 wherein the volume of the mixture of capping reagents is modified independently for each cycle of steps b) through e) such that about 8.5 equivalents of acetic anhydride are used for the first cycle and over each successive cycle that includes the capping step e) the equivalents of acetic anhydride are serially reduced to about 1 equivalent based on the loading of the solid support.

18. The method claim 1 wherein the volume of the mixture of capping reagents is modified independently for each cycle of steps b) through e) such that about 4 equivalents of acetic anhydride are used for the first cycle and over each successive cycle that includes the capping step e) the equivalents of acetic anhydride are serially reduced to about 1 equivalent based on the loading of the solid support.

19. The method of claim 1 wherein the mixture of capping reagents comprises from about 5% to about 10% acetic anhydride, from about 5% to about 10% N-methylimidazole and from about 5% to about 15% pyridine or from about 5% to about 10% 2,6-lutidine dissolved in tetrahydrofuran, toluene or acetonitrile.

20. The method claim 1 wherein the mixture of capping reagents comprises from about 5% to about 10% acetic anhydride, from about 5% to about 10% N-methylimidazole and from about 5% to about 15% pyridine in toluene.

21. The method of claim 1 wherein the mixture of capping reagents comprises from 10% acetic anhydride, about 10% N-methylimidazole and about 15% pyridine in toluene.

22. The method of claim 1 wherein the oligomeric compound comprises from about 10 to about 40 monomer subunits in length.

* * * * *